(12) United States Patent
Kimchi et al.

(10) Patent No.: US 9,149,523 B2
(45) Date of Patent: Oct. 6, 2015

(54) COMPOSITIONS AND METHODS FOR TREATING CANCER AND NEURODEGENERATIVE DISEASES

(75) Inventors: Adi Kimchi, Rehovot (IL); Rodrigo Carlessi, Rehovot (IL)

(73) Assignee: Yeda Research and Development Co. Ltd., Rehovot (IL)

(*) Notice: Subject to any disclaimer, the term of this patent is extended or adjusted under 35 U.S.C. 154(b) by 12 days.

(21) Appl. No.: 13/995,096

(22) PCT Filed: Dec. 14, 2011

(86) PCT No.: PCT/IL2011/000950
§ 371 (c)(1),
(2), (4) Date: Jun. 17, 2013

(87) PCT Pub. No.: WO2012/081017
PCT Pub. Date: Jun. 21, 2012

(65) Prior Publication Data
US 2013/0266582 A1    Oct. 10, 2013

Related U.S. Application Data

(60) Provisional application No. 61/423,100, filed on Dec. 15, 2010.

(51) Int. Cl.
| | |
|---|---|
| G01N 33/533 | (2006.01) |
| G01N 33/535 | (2006.01) |
| G01N 33/483 | (2006.01) |
| C12N 9/00 | (2006.01) |
| A61K 39/395 | (2006.01) |
| G01N 33/50 | (2006.01) |
| C12Q 1/48 | (2006.01) |

(52) U.S. Cl.
CPC ............ *A61K 39/3955* (2013.01); *C12Q 1/485* (2013.01); *G01N 33/5011* (2013.01); *G01N 33/5058* (2013.01); *G01N 2333/9121* (2013.01)

(58) Field of Classification Search
None
See application file for complete search history.

(56) References Cited

FOREIGN PATENT DOCUMENTS

| | | |
|---|---|---|
| WO | 95/010630 | 4/1995 |
| WO | 2004/048531 | 6/2004 |
| WO | 2004/108083 | 12/2004 |
| WO | 2008/066878 | 6/2008 |
| WO | 2008/108964 | 9/2008 |
| WO | 2009/023725 | 2/2009 |
| WO | 2009/117346 | 9/2009 |
| WO | 2009/120249 | 10/2009 |

OTHER PUBLICATIONS

Shamloo et al., Death-associated Protein Kinase Is Activated by Dephosphorylation in Response to Cerebral Ischemia. The Journal of Biological Chemistry vol. 280, No. 51, pp. 42290-42299, Dec. 23, 2005.*

(Continued)

*Primary Examiner* — Gregory S Emch
*Assistant Examiner* — Aurora M Fontainhas

(57) ABSTRACT

The present invention relates to compositions and methods for regulating ROC-mediated death-associated protein kinase (DAPk) activity. The compositions and methods of the present invention are useful for treating or ameliorating cancer as well as pathologies associated with neuronal cell death, such as epilepsy and hypoxia/ischemia acute brain injury. The present invention further relates to screening methods for identifying agents that regulate ROC-mediated DAPk activation.

2 Claims, 10 Drawing Sheets

(56) References Cited

OTHER PUBLICATIONS

Bialik and Kimchi (2004) DAP-kinase as a target for drug design in cancer and diseases associated with accelerated cell death. Semin Cancer Biol 14(4): 283-94.

Bialik and Kimchi (2006) The death-associated protein kinases: structure, function, and beyond. Annu Rev Biochem 75: 189-210.

Chen et al., (2005) Bidirectional signals transduced by DAPK-ERK interaction promote the apoptotic effect of DAPK. EMBO J 24(2):294-304.

Cohen et al., (1997) DAP-kinase is a Ca2+/calmodulin-dependent, cytoskeletal-associated protein kinase, with cell death-inducing functions that depend on its catalytic activity. EMBO J 16(5): 998-1008.

Dächsel and Farrer (2010) LRRK2 and Parkinson disease. Arch Neurol 67(5): 542-7.

de Diego et al., (2010) Molecular basis of the death-associated protein kinase-calcium/calmodulin regulator complex. Sci Signal 3(106): ra6.

Deiss et al., (1995) Identification of a novel serine/threonine kinase and a novel 15-kD protein as potential mediators of the gamma interferon-induced cell death. Genes Dev 9(1): 15-30.

Deng et al., (2008) Structure of the ROC domain from the Parkinson's disease-associated leucine-rich repeat kinase 2 reveals a dimeric GTPase. Proc Natl Acad Sci U S A 105(5): 1499-504.

Gozuacik et al., (2008) DAP-kinase is a mediator of endoplasmic reticulum stress-induced caspase activation and autophagic cell death. Cell Death Differ 15(12): 1875-86.

Greggio et al., (2008) The Parkinson disease-associated leucine-rich repeat kinase 2 (LRRK2) is a dimer that undergoes intramolecular autophosphorylation. J Biol Chem 283(24): 16906-14.

Guo et al., (2007) The Parkinson's disease-associated protein, leucine-rich repeat kinase 2 (LRRK2), is an authentic GTPase that stimulates kinase activity. Exp Cell Res 313(16): 3658-70.

Henshall et al., (2004) Death-associated protein kinase expression in human temporal lobe epilepsy. Ann Neurol 55(4): 485-94.

Inbal et al., (1997) DAP kinase links the control of apoptosis to metastasis. Nature 390(6656): 180-4.

Ito et al., (2007) GTP binding is essential to the protein kinase activity of LRRK2, a causative gene product for familial Parkinson's disease. Biochemistry 46(5): 1380-8.

Kissil et al.' (1997) DAP-kinase loss of expression in various carcinoma and B-cell lymphoma cell lines: possible implications for role as tumor suppressor gene. Oncogene 15(4): 403-7.

Klein et al., (2009) Homo- and heterodimerization of ROCO kinases: LRRK2 kinase inhibition by the LRRK2 ROCO fragment. J Neurochem 111(3): 703-15.

Koren et al., (2010) DAP1, a novel substrate of mTOR, negatively regulates autophagy. Curr Biol 20(12): 1093-8.

Llambi et al., (2005) The dependence receptor UNC5H2 mediates apoptosis through DAP-kinase. EMBO J 24(6): 1192-201.

Marin et al., (2008) The Roco protein family: a functional perspective. FASEB J 22(9): 3103-10.

Pelled et al., (2002) Death-associated protein (DAP) kinase plays a central role in ceramide-induced apoptosis in cultured hippocampal neurons. J Biol Chem 277(3): 1957-61.

Raval et al., (2007) Downregulation of death-associated protein kinase 1 (DAPK1) in chronic lymphocytic leukemia. Cell 129(5): 879-90.

Raveh et al., (2001) DAP kinase activates a p19ARF/p53-mediated apoptotic checkpoint to suppress oncogenic transformation. Nat Cell Biol 3(1): 1-7.

Schori et al., (2002) Immune-related mechanisms participating in resistance and susceptibility to glutamate toxicity. Eur J Neurosci 16(4): 557-64.

Shani et al., (2004) Death-associated protein kinase phosphorylates ZIP kinase, forming a unique kinase hierarchy to activate its cell death functions. Mol Cell Biol 24(19): 8611-26.

Shohat et al., (2001) The pro-apoptotic function of death-associated protein kinase is controlled by a unique inhibitory autophosphorylation-based mechanism. J Biol Chem 276(50): 47460-7.

Tu et al., (2010) DAPK1 interaction with NMDA receptor NR2B subunits mediates brain damage in stroke. Cell 140(2): 222-34.

Velentza et al., (2003) An aminopyridazine-based inhibitor of a pro-apoptotic protein kinase attenuates hypoxia-ischemia induced acute brain injury. Bioorg Med Chem Lett 13(20): 3465-70.

Widau et al., (2010) Protein phosphatase 2A (PP2A) holoenzymes regulate death-associated protein kinase (DAPK) in ceramide-induced anoikis. J Biol Chem . Apr. 30, 2010;285(18):13827-38.

Larova: "Guanosine 5'-Triphosphate, GTP", Feb. 17, 2010, XP55021862, URL:http://www.larova.com/images/2e9e2ca4ee/NU-1012-1yophil.pdf (retreived on Mar. 14, 2012) abstract.

\* cited by examiner

COMPOSITIONS AND METHODS FOR TREATING CANCER AND NEURODEGENERATIVE DISEASES

RELATED APPLICATION DATA

This application is the U.S. National Stage of International Application No. PCT/IL2011/000950, filed Dec. 14, 2011, which claims the benefit of U.S. Provisional Application No. 61/423,100, filed Dec. 15, 2010, the contents of each of which are herein expressly incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 15,109 byte ASCII (text) file named "Seq_List" created on Jun. 17, 2013.

FIELD OF THE INVENTION

The present invention relates to compositions and methods for regulating death-associated protein kinase (DAPk) activity. The compositions and methods of the present invention are useful for treating or ameliorating cancer as well as pathologies associated with neuronal cell death, such as epilepsy, hypoxia/ischemia and acute brain injury. The present invention further relates to screening methods for identifying agents that regulate DAPk activation.

BACKGROUND OF THE INVENTION

Death-associated protein kinase (DAPk, DAPk-1) is a Ser/Thr kinase with a multiple domain structure (Bialik and Kimchi 2006). Its catalytic domain is located at the extreme N-terminus, and is followed by a $Ca^{2+}$/calmodulin (CaM) regulatory domain. DAPk has been shown to be activated by two complementary mechanisms that serve to release the auto-inhibitory functions of this regulatory domain. One mechanism involves dephosphorylation of an inhibitory auto-phosphorylation at a critical Serine (Ser) at position 308 within the CaM regulatory domain which increases its affinity for CaM and also enhances the CaM-independent catalytic activity (Shohat, Spivak-Kroizman et al. 2001). The second involves the binding of calcium-activated CaM to the CaM regulatory domain, which results in the removal of this inhibitory domain from the catalytic cleft (Cohen, Feinstein et al. 1997) and which in turn further prevents Ser 308 negative auto-phosphorylation. Recently, the crystal structure of the binary DAPk-CaM complex has been resolved (de Diego, Kuper et al.) and the phosphatase responsible for Ser 308 dephosphorylation and DAPk activation was identified (Gozuacik, Bialik et al. 2008; Widau, Jin et al. 2010).

Other structural motifs within DAPk include a series of eight ankyrin repeats which follow the catalytic domain, after which is a region that has been shown to direct the kinase to the actin cytoskeleton (Bialik, Bresnick et al. 2004).

A putative P-loop motif which resides at amino acids 695-702 of DAPk, partially overlapping the cytoskeletal interacting domain, has been previously documented (Deiss, Feinstein et al. 1995). Yet the cellular and biochemical functions of this P-loop have not been studied so far.

The C-terminus region of DAPk contains a death domain, followed by a 17 amino acid tail rich in Ser residues (Bialik and Kimchi 2006). Several proteins have been reported to interact with the death domain of DAPk including binding to the death domain of UNC5H2 (Llambi, Lourenco et al. 2005).

An increasing amount of evidence supports the idea that DAPk works as a tumor suppressor gene in vivo. It was first noticed that DAPk mRNA and protein expression are lost in various types of cancer cell lines (Kissil, Feinstein et al. 1997). Later on, many studies have been published showing DAPk promoter hypermethylation and consequent expression silencing in tumors that had been freshly isolated from patients (Bialik and Kimchi 2004; Bialik, and Kimchi 2006). In addition, a germline mutation in DAPk was found in cases of familial chronic lymphocytic leukemia (CLL), where a single nucleotide change causes a predisposition to CLL (Raval, Tanner et al. 2007). In experimental systems it was reported that DAPk is capable of blocking tumor metastasis in vivo (Inbal, Cohen et al. 1997) and suppressing oncogenic transformation induced by c-myc and E2F in vitro (Raveh, Droguett et al. 2001). Altogether, these data established the tumor suppressive functions of DAPk, explaining why this gene is subjected to inactivation or loss during tumor development.

International Patent Application Publication No. WO 09/120,249 relates to detection of cell proliferative disorders, particularly head and neck cancer, utilizing analysis of the methylation state of targeted genes or regulatory regions of genes, including DAPk. Additional patent applications disclosing DAPk as a marker for diagnosing cancer include, inter alia, WO 09/117,346; WO 09/023,725 and WO 08/066,878.

International Patent Application Publication No. WO 08/108,964 is directed to compounds useful as selective kinase inhibitors, particularly DAPk-1 inhibitors, methods for producing such compounds and methods for treating or ameliorating chronic lymphocytic leukemia. WO 08/108,964 is further directed to methods for determining susceptibility to chronic lymphocytic leukemia in a subject includes determining a loss or reduced expression of DAPk-1 or fragments or functional equivalents thereof.

International Patent Application Publication No. WO 04/108083 relates to the treatment of malignancies by selectively inducing apoptosis. Certain aspects of the '083 publication relate to DNA methylation antagonists administered in an amount sufficient to induce expression of DAPk.

International Patent Application Publication No. WO 04/048531 provides compounds, compositions and methods for modulating the expression of DAPk-1. In particular, the '531 publication provides compounds, particularly oligo-nucleotide compounds, which hybridize with nucleic acid molecules encoding DAPk-1 and modulate DAPk-1 expression.

International Patent Application Publication No. WO 95/010630, to one of the inventors of the present application and others, relates to death protein (DAP) genes and DAP products for promoting death of normal or tumor cells, particularly in therapy of diseases or disorders associated with uncontrolled, pathological cell growth, e.g. cancer or psoriasis.

Gain of function of DAPk, on the other hand, has been reported to be involved in several pathologies associated with neuronal cell death such as epilepsy (Henshall, Schindler et al. 2004) and hypoxia/ischemia acute brain injury (Velentza, Wainwright et al. 2003). This was strongly supported by a recent publication showing that ischemic injury by excessive activation of NMDA glutamate receptors promotes the association of DAPk to these receptors and that disrupting this association reduces damage to the brain (Tu, Xu et al. 2010). Notably, the functional link of DAPk to different types of neuronal cell death is consistent with previous studies documenting that neurons lacking DAPk are more resistant to various death insults compared to the wild type counterparts. This was shown both in primary cultures of neurons (prepared from the DAPk knockout mice generated) and in animal model system (Pelled, Raveh et al. 2002; Schori, Yoles et al. 2002). All these studies point at the major functional role that DAPk may exert in life and death decisions of neuronal cells and make DAPk an attractive novel target for neurodegenerative drug discovery. Thus, the mechanisms of DAPk activation and regulation in cells have to be comprehended thoroughly in order for the selective inhibition of this kinase activity to be used in the treatment of such diseases.

It is noteworthy that a novel protein family was described recently, called the ROCO family (Marin, van Egmond et al. 2008). The family members, mostly comprising protein kinases, contain two common domains, the ROC (Ras of complex proteins) domain, which shares similarity with Ras and other related GTPases, and the COR (C-terminal of Roc) domain that locates downstream from the ROC domain in all members of the family. The most famous of these proteins is Leucine Repeat Rich Kinase 2 (LRRK2), a kinase implicated in Parkinson's disease. In fact, mutations in LRRK2 are the most common genetic causes of both familial and sporadic cases of late-onset Parkinson's disease (Dachsel and Farrer 2010). LRRK2's ROC domain, when bound to Guanosine-5'-triphosphate (GTP), mediates its homo-dimerization and activates the catalytic activity of the downstream kinase domain (Guo, Gandhi et al. 2007; Ito, Okai et al. 2007; Deng, Lewis et al. 2008; Greggio, Zambrano et al. 2008). Interestingly, DAPk contains a region with a significant homology to the ROC-COR domains, which includes the P-loop and cytoskeletal-targeting domain (Marin, van Egmond et al. 2008; Klein, Rovelli et al. 2009).

None of the background art, however, discloses or suggests agents which can mediate DAPk activity via the ROC domain. Such agents are, therefore, particularly useful in treating or ameliorating cell proliferative diseases (e.g., cancer) or neurodegenerative diseases such as pathologies associated with neuronal cell death.

There exists a long-felt need for more effective means of curing or ameliorating cancer and neurodegenerative diseases. The development of novel agents capable of selectively regulating DAPk activity is therefore desirable.

SUMMARY OF THE INVENTION

The present invention provides compositions and methods for modulating death-associated protein kinase (DAPk) activity via the newly identified ROC (Ras of complex proteins) domain. The compositions and methods of the present invention are therefore useful for treating or ameliorating cancer. In addition, the compositions and methods of the present invention are useful for treating or preventing neurodegenerative diseases, particularly pathologies associated with neuronal cell death, such as epilepsy, hypoxia/ischemia and acute brain injury. The present invention further provides methods of screening for agents capable of regulating ROC-mediated DAPk activation.

It is disclosed herein for the first time that DAPk undergoes homo-oligomerization, mediated by the ROC domain, residing between amino acids 667-954 of human DAPk. Notably, the deletion of the ROC domain did not reduce, but rather increase the catalytic activity of DAPk.

It is further disclosed for the first time that the ROC domain confers the capability of GTP binding via a P-Loop motif located at the N-terminus of said ROC domain. Furthermore, upon GTP binding, the ROC domain negatively regulates DAPk catalytic activity in an intra-molecular signal transduction mode. These findings are particularly unexpected since GTP-binding to the ROC domain of other proteins (e.g., the Leucine Repeat Rich Kinase 1 and 2) was shown to positively regulate their kinase catalytic activity. Surprisingly, said GTP binding affects the status of a critical inhibitory autophosphorylation in DAPk at Ser 308, thus controlling its catalytic activity. Furthermore, it is demonstrated hereinbelow that GTP binding to the ROC domain regulates DAPk's cellular function in vivo.

The amino acid sequence of human DAPk-1 polypeptide (Accession No.: NP_004929) is set forth as SEQ ID NO: 3. The ROC domain of DAPk is about 287 amino acid long and in particular embodiments resides between amino acid 667-954 of human DAPk. In a specific embodiment, the ROC domain consists of the amino acid sequence as set forth in SEQ ID NO: 1. The P-Loop motif is located at the N-terminus of said ROC domain, and in particular embodiments has the amino acid sequence as set forth as SEQ ID NO: 2 (GHSGSGKTT).

Thus, the present invention provides screening assays for identifying agents that bind and modulate the activity of ROC domain thereby regulating DAPk activity. In one embodiment, the invention provides screening assays for identifying agents that regulate ROC-mediated DAPk homo-oligomerization. In additional embodiments, the invention provides screening assays for identifying agents that regulate GTPase activity of DAPk, e.g., GTP binding to the ROC domain of DAPk, or alternatively GTP dissociation from the ROC domain of DAPk. Particularly, GTPase activity of DAPk is determined by the agent's ability to regulate GTP binding to the P-Loop motif residing at amino acids 695-702 of DAPk. In some embodiments, DAPk activity is detected by the ability of a putative agent to alter the phosphorylation state of the Serine residue in position 308 of DAPk (SEQ ID NO: 3). The present invention further provides compositions and methods for mediating DAPk activity via the ROC domain, specifically by affecting GTP binding to the P-Loop motif within the ROC domain, thereby being useful in treating or ameliorating cancer as well as neurodegenerative diseases.

According to a first aspect, the present invention provides a method of screening for an anti cancer agent, comprising:
  (a) exposing a cell expressing death-associated protein kinase (DAPk) to a putative anti-cancer agent;
  (b) determining the promotion of DAPk activation mediated by binding of the agent to the ROC domain of DAPk;
  wherein promotion of DAPk activation indicates that said agent is an anti-cancer agent.

In a specific embodiment, the determining the promotion of DAPk activation is in the presence and absence of said agent, wherein a significant promotion in DAPk activity indicates that said agent is an anti-cancer agent.

According to one embodiment, said promotion of DAPk activation is determined by the agent's ability to negatively affect GTP binding to the ROC domain of DAPk. In some embodiments, negatively affecting GTP binding to the ROC domain is selected from the group consisting of: preventing GTP binding to said ROC domain, enhancing GTP hydrolysis from said ROC domain, and enhancing GTP dissociation from said ROC domain of DAPk, wherein each possibility is a separate embodiment of the invention. According to a particular embodiment, said promotion of DAPk activation is determined by the ability of the agent to prevent GTP binding to the ROC domain of DAPk.

GTP binding to the ROC domain is, in certain embodiments of the invention, GTP binding to the P-Loop motif located within the ROC domain. In one embodiment, said P-Loop motif has the amino acid sequence as set forth in SEQ ID NO: 2.

According to another embodiment, said promotion of DAPk activation is determined by the ability of the agent to inhibit DAPk homo-oligomerization. According to another embodiment, said promotion of DAPk activation is determined by the ability of said agent to affect at least one phenotypic effect selected from the group consisting of: cell rounding, cell detachment, and membrane blebbing.

According to specific embodiments, the putative agent is selected from the group consisting of: amino acids, peptides, nucleic acids, organic molecules, inorganic compounds and antibodies. Each possibility is a separate embodiment of the invention.

According to some embodiments, the present invention provides an anti-cancer agent obtained by said screening method of the invention, wherein the agent promotes ROC-mediated activation of DAPk. According to some specific embodiments the agent binds to the P-Loop motif within the ROC domain. According to additional embodiments, the present invention provides a pharmaceutical composition comprising said anti cancer agent as an active ingredient, and a pharmaceutically acceptable carrier.

According to another aspect, the present invention provides a method of screening for an agent for treating pathologies associated with neuronal cell death, comprising:
(a) exposing a cell expressing DAPk to a putative agent;
(b) determining the inhibition or reduction of DAPk activation mediated by the binding of the agent to the ROC domain of DAPk;
wherein inhibition or reduction of DAPk activation indicates that said agent is capable of treating pathologies associated with neuronal cell death.

In a specific embodiment, the determining the inhibition or reduction of DAPk activation is in the presence and absence of said agent, wherein a significant inhibition or reduction in DAPk activity indicates that said agent is useful in treating pathologies associated with neuronal cell death. According to some embodiments, said inhibition or reduction of DAPk activation is determined the agent's ability to positively affect GTP binding to the ROC domain of DAPk. In some embodiments, positively affecting GTP binding to the ROC domain is selected from the group consisting of: enhancing GTP binding to the ROC domain, preventing GTP hydrolysis from the ROC domain and preventing GTP dissociation from the ROC domain of DAPk, wherein each possibility is a separate embodiment of the invention. According to a particular embodiment, said inhibition or reduction of DAPk activation is determined by the ability of the agent to enhance GTP binding to the ROC domain of DAPk.

According to specific embodiments, said inhibition or reduction of DAPk activation is determined by the ability of the agent to enhance DAPk homo-oligomerization.

According to another embodiment, the putative agent is selected from the group consisting of: amino acids, peptides, nucleic acids, organic molecules, inorganic compounds and antibodies. Each possibility is a separate embodiment of the invention.

According to another embodiment, the present invention provides an agent useful for treating pathologies associated with neuronal cell death, the agent being obtained by the screening method of the invention, wherein said agent inhibits or reduces ROC-mediated activation of DAPk. According to another embodiment, the present invention provides a pharmaceutical composition comprising said agent as an active ingredient, and a pharmaceutically acceptable carrier.

According to another aspect, the present invention provides an agent capable of modulating DAPk activity, wherein DAPk activity is modulated in a ROC dependent manner. In a particular embodiment, the agent is capable of binding the ROC domain of DAPk, or a fragment thereof.

In another embodiment, the agent binds the P-Loop motif within said ROC domain. In another embodiment, the agent regulates DAPk GTPase activity, particularly, GTP binding to the ROC domain, or particularly to the P-Loop motif. In certain embodiments, the ROC domain has the amino acid sequence as set forth in SEQ ID NO: 1. In some embodiments, the P-Loop motif has the amino acid sequence as set forth in SEQ ID NO: 2.

According to some embodiments, modulating DAPk activity comprises promoting DAPk activation. According to one embodiment, the agent promotes DAPk activity by negatively affecting GTP binding to the ROC domain of DAPk. Negatively affecting GTP binding to the ROC domain (thereby promoting DAPk activation) is, in certain embodiments, selected from the group consisting of: preventing GTP binding to said ROC domain, enhancing GTP hydrolysis from said ROC domain (e.g., through a GTPase-activating protein (GAP)), and enhancing GTP dissociation from said ROC domain of DAPk, wherein each possibility is a separate embodiment of the invention. According to a specific embodiment, the agent prevents GTP binding to the ROC domain of DAPk, preferably to the P-Loop motif. According to another embodiment, the agent inhibits DAPk homo-oligomerizatio. According to another embodiment, the agent is capable of promoting cell rounding, cell detachment, and membrane blebbing.

According to other embodiments, modulating DAPk activity comprises inhibiting or reducing DAPk activation. According to one embodiment, the agent inhibits or reduces DAPk activity by positively affecting GTP binding to the ROC domain of DAPk. Positively affecting GTP binding to the ROC domain (thereby inhibiting or reducing DAPk activation) is in certain embodiments, selected from the group consisting of: enhancing GTP binding to the ROC domain, preventing GTP hydrolysis from the ROC domain and preventing GTP dissociation from the ROC domain of DAPk, wherein each possibility is a separate embodiment of the invention. According to another embodiment, the agent enhances DAPk homo-oligomerization.

According to another aspect, the present invention provides a pharmaceutical composition comprising as an active ingredient an agent capable of modulating DAPk activity in a ROC dependent manner, and a pharmaceutically acceptable carrier.

According to one embodiment, the agent promotes ROC-mediated DAPk activation. Typically, promoting DAPk activation is beneficial in the treatment of proliferative diseases such as cancer.

According to other embodiments, the agent inhibits or reduces ROC-mediated DAPk activation. Typically, inhibiting DAPk activity is beneficial in the treatment of pathologies associated with neuronal cell death.

According to an additional aspect, the present invention provides a method for treating a proliferative disease (e.g., cancer) in a subject in need thereof, comprising administering to the subject a therapeutically effective amount of a pharmaceutical composition comprising an active ingredient capable of promoting ROC-mediated DAPk activation.

According to one embodiment, the proliferative disease is cancer. According to certain embodiments, the cancer to be treated is selected from the group consisting of prostate cancer, breast cancer, skin cancer, colon cancer, lung cancer, pancreatic cancer, head and neck cancer, kidney cancer, ovarian cancer, cervix cancer, bone cancer, liver cancer, thyroid cancer, brain cancer, lymphoma, myeloma and leukemia.

According to certain embodiments, the proliferative disease is a hematopoietic malignancy, such as lymphoma and leukemia. According to particular embodiments, the hematopoietic malignancy is selected from the group consisting of: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to another embodiment, the proliferative disease is a solid malignancy. According to particular embodiments, the solid malignancy is selected from the group consisting of: prostate cancer, breast cancer, skin cancer, colon cancer, lung cancer, pancreatic cancer, head and neck cancer, kidney cancer, ovarian cancer, cervix cancer, bone cancer, liver cancer, thyroid cancer and brain cancer.

According to an additional aspect, the present invention provides a method for treating a pathology associated with neuronal cell death, comprising administering to the subject a therapeutically effective amount of a pharmaceutical composition comprising an active ingredient capable of inhibiting or reducing ROC-mediated DAPk activation.

According to another embodiment, the pathology associated with neuronal cell death is selected form the group consisting of: epilepsy, hypoxia/ischemia acute brain injury, Parkinson's disease and Alzheimer's disease.

According to some embodiments of the present invention, the agent is administered ex vivo. According to other embodiment of the invention, the agent is administered in vivo.

According to an additional aspect, the present invention provides a method for regulating ROC-mediated DAPk activity. In some embodiments, said DAPk activity regulation comprises targeting the ROC domain. In a particular embodiment, targeting the ROC domain refers to targeting the P-loop residing in the ROC domain.

According to one embodiment, targeting the ROC domain inhibits DAPk homo-oligomerization. According to another embodiment, targeting the ROC domain prevents GTP binding to DAPk. As disclosed herein, inhibiting DAPk homo-oligomerization and/or preventing GTP binding to DAPk promote DAPk activation thereby being beneficial in the treatment of proliferative diseases such as cancer.

According to another embodiment, targeting the ROC domain enhances DAPk homo-oligomerization. According to another embodiment, targeting the ROC domain leads to enhancement of GTP binding to DAPk, prevention of GTP hydrolysis, or prevention of GTP dissociation from DAPk, wherein each possibility is a separate embodiment of the present invention. As disclosed herein, enhancing DAPk homo-oligomerization and/or enhancement of GTP binding to DAPk promote DAPk activation thereby being beneficial in the treatment of pathologies associated with neuronal cell death.

According to another aspect, the present invention provides a method of screening an agent for its ability to modulate DAPk activity, comprising the steps of:
  (a) exposing a cell expressing DAPk to a putative agent;
  (b) determining DAPk activity mediated by GTP binding to the ROC domain of DAPk in the presence and absence of said agent;

wherein a significant change in GTP binding to the ROC domain of DAPk in the presence of said agent, indicates that said agent is DAPk-modulating agent.

According to a particular embodiment, DAPk activity is DAPk catalytic activity. In one embodiment, DAPk catalytic activity is the phosphorylation of the Serine residue in position 308 of DAPk. In another embodiment, DAPk has an amino acid sequence as set forth in SEQ ID NO:3. According to another particular embodiment, said DAPk catalytic activity is selected from apoptosis and autophagic cell death.

According to some embodiments, modulating DAPk activity is promoting DAPk activity. According to another embodiment, GTP binding to the ROC domain of DAPk is reduced or prevented. According to another embodiment, said agent is an anti-cancer agent.

According to some embodiments, modulating DAPk activity is reducing or inhibiting DAPk activity. According to another embodiment, GTP binding to the ROC domain of DAPk is enhanced. According to another embodiment, said agent is capable of treating pathologies associated with neuronal cell death.

According to an additional aspect, the present invention provides an active ingredient capable of promoting ROC-mediated DAPk activation for use in treating a proliferative disease (e.g., cancer) in a subject in need thereof. According to another embodiment, the present invention provides an active ingredient capable of promoting ROC-mediated DAPk activation for use in the preparation of a medicament for treating a proliferative disease (e.g., cancer) in a subject in need thereof. According to another embodiment, the present invention provides a pharmaceutical composition comprising said agent and a pharmaceutically acceptable carrier.

According to an additional aspect, the present invention provides an active ingredient capable of inhibiting or reducing ROC-mediated DAPk activation for use in treating a associated with neuronal cell death in a subject in need thereof. According to another embodiment, the present invention provides an active ingredient capable of inhibiting or reducing ROC-mediated DAPk activation for use in the preparation of a medicament for treating associated with neuronal cell death in a subject in need thereof. According to another embodiment, the present invention provides a pharmaceutical composition comprising said agent and a pharmaceutically acceptable carrier.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description

BRIEF DESCRIPTION OF THE DRAWINGS

FIG. 1A, Cells were co-transfected with both hemaglutinin (HA)-DAPk and Flag-DAPk or with HA-DAPk only. FIG. 1B, Cells were co-transfected either with HA-DAPk and Flag-DAPk or HA-DAPk and DAP1-Flag as a non relevant control. The cells were lysed and anti-Flag immunoprecipitations (IP-α Flag) were performed. Immune complexes were analyzed by western blot alongside aliquots of total cell extracts (FIGS. 1A-B). FIG. 1C, Extracts of cells, transfected with Flag-DAPk, were immuneprecipitated with anti-Flag beads and Flag-DAPk was eluted by competition with Flag peptide, to test the purification status prior to column injection. FIG. 1D, Size exclusion chromatogram of immunopurified Flag-DAPk detected by UV absorbance at 280 nm. FIG. 1E, Selected fractions from the size exclusion chromatography were collected and analyzed by western blot with anti-Flag antibodies.

FIG. 2A, Schematic representation of the different DAPk constructs utilized for mapping DAPk homo-oligomerization. The indicated domains: Kinase domain (KD); $Ca^{+2}$/Calmodulin binding region (CaM); Ankyrin repeats (AK); P-Loop; Ras of complex proteins domain (ROC); C-terminal of ROC domain (COR); Death domain (DD); and Serine (Ser) rich tail. FIG. 2B, HEK 293T cells were co-transfected with HA-DAPk along with either Flag-ROC fragment or DAP1-Flag. Immunoprecipitation with anti-Flag beads (IP-α-Flag) was performed and immuno-complexes and cell extracts were analyzed by western blot. FIG. 2C, Cells co-transfected with Flag-DAPk and one of the different HA-tagged DAPk constructs, namely HA-DAPk (WT), HA-ΔROC—a deletion between amino acids 667-954; HA-ΔKinase—a N-terminal deletion (1-285); and ΔROC/ΔKinase—deletion of both KD (1-285) and ROC domain (667-954). Immunoprecipitation and western blot were performed as in B. FIG. 2D, Cells co-transfected with Flag-ROC and HA-ROC; HA-ROC and Flag-ROC-Δ-P-loop; Flag-ROC and HA-DAPk (WT); Flag-ROC-Δ-P-Loop and HA-DAPk (WT); or HA-ROC and DAP1-Flag.

FIG. 3A, western blot analysis showing the expression levels of the different constructs in cell extracts. FIG. 3B, western blot analysis showing the eluted material from the GTP-agarose beads. DAPk WT, but not ΔCyto and ΔP-Loop binds specifically to the GTP-agarose beads.

FIG. 4A, the catalytic activity of ΔROC mutant was compared with that of DAPk WT. FIG. 4B, the catalytic activity of other two mutants that abolish GTP-binding, ΔP-Loop and T701N were compared to that of DAPk WT. FIG. 4C, The effect of pre-incubation of DAPk WT with either GDP or Gpp(NH)p prior to catalytic activity measurement was determined. FIG. 4D, DAPk WT and ΔP-Loop were assayed with non-limiting amounts of hMLC (1 μg).

FIG. 5A, HEK293T cells were transfected either with Flag-DAPk WT or with Flag-ΔP-Loop mutant. Cell extracts were analyzed by western blot and the phosphorylation status of the Ser 308 was assessed with a mouse monoclonal antibody that recognizes only the phosphorylated version of DAPk Ser 308. FIG. 5B, HEK293T cells were co-transfected with DAPk kinase dead (HA-K42A) and increasing amounts of GFP-DAPk. Cells were lysed and total cell extracts were analyzed by western blot with antibodies against total DAPk (α-DAPk55) and phosphorylated Ser308.

FIG. 6A, Western blot analysis showing the expression levels of the different constructs. FIG. 6B, bars graph representing the percentage of cell detachment 24 h post-transfection in comparison with Luciferase transfected cells. C, Fluorescence microscope analysis of membrane blebbing.

DETAILED DESCRIPTION OF THE INVENTION

Figure 1A:
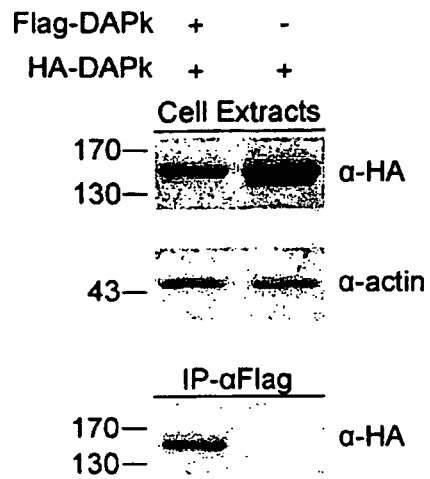
FIGS. 1A-E demonstrates DAPk oligomerizes in HEK 293T cells.

The present invention provides screening assays for identifying agents that modulate the activity of ROC domain and, therefore, regulate the activity of DAPk. The screening assays of the invention are useful in identifying agents that regulate ROC-mediated DAPk homo-oligomerization and/or regulate GTP binding or dissociation to the ROC domain of DAPk. The present invention further provides compositions and methods capable of mediating DAPk activity via the ROC domain, thereby being useful in treating or ameliorating cancer as well as pathologies associated with neuronal cell death.

As exemplified hereinbelow, the ROC domain of DAPk was found to be a functional domain mediating GTP binding and homo-oligomerization of DAPk, thereby specifically regulating DAPk activity. Particularly, it was found that DAPk binds GTP through a P-Loop motif (SEQ ID NO: 2) located at the ROC domain's N-terminal end. Surprisingly, GTP-binding at the P-Loop has a negative impact on the catalytic activity of DAPk, which is in contrast to GTP-binding at the ROC domain of other members of the ROCO family (e.g., the LRRK1 and LRRK2) which activates their kinase catalytic activity.

The agents of the present invention are capable of binding the ROC domain of DAPk and consequently modulate DAPk activity. Modulating DAPk activity, in some embodiment, relates to promoting DAPk activation. In other embodiments, modulating DAPk activity relates to inhibiting DAPk activation In some embodiments, DAPk activity relates to the phosphorylation of the Serine residue in position 308 of DAPk (SEQ ID NO: 3).

"ROC-mediated DAPk activation" or "mediating DAPk activity via the ROC domain" refers to a biological or biochemical activity of DAPk that results from, and/or is mediated by, the ROC domain. Preferably, DAPk activity according to the present invention relates to DAPk catalytic activity known in the art to participate in programmed cell death pathways, such as, apoptosis and autophagic cell death.

As used herein "inhibiting ROC-mediated activation of DAPk" (or interchangeably "inhibit" and "inhibition") or "reducing ROC-mediated activation of DAPk" means to decrease DAPk activity mediated by its ROC domain (such as by binding of the agent to the ROC domain). This can include but is not limited to the complete ablation of the activity, or alternatively, a 10% reduction in DAPk activity as compared to the native DAPk activity. Thus, the reduction can be a 10, 20, 30, 40, 50, 60, 70, 80, 90, 100%, or any amount of reduction in between the specifically recited percentages, as compared to native or control levels.

As used herein "promoting ROC-mediated activation of DAPk" (or interchangeably "promotion" and "promote") refer to an increase in DAPk activity mediated by its ROC domain (such as by binding of the agent to the ROC domain). This can include but is not limited to turning on DAPk activity, or initiating DAPk activity. This may also include, for example, a 10% increase in DAPk activity. Thus, the increase in DAPk activity, can be a 10, 20, 30, 40, 50, 60, 70, 80, 90, 100%, or more, including any amount of increase in between the specifically recited percentages, as compared to native or control levels.

As used herein, the term "significant" (such as in a "significant change in GTP binding" or "significant inhibition or reduction in DAPk activity" or "significant promotion in DAPk activity") refers, in different embodiments, to a statistically significant difference, or in other embodiments to a significant difference as recognized by a skilled artisan.

"DAPk homo-oligomerization" as used here relates to the association of at least two DAPk proteins. Methods for detection of protein (e.g. DAPk) homo-oligomerization are known in the art and are demonstrated hereinbelow (e.g. Example 1). Method for determining GTP binding to a polypeptide (such as the ROC domain of DAPk) are known in the art, as well as demonstrated herein-below (e.g. Example 3).

Pharmaceutical Compositions

According to some embodiments, the present invention provides a pharmaceutical composition comprising as an active ingredient an agent capable of regulating ROC-mediated DAPk activity, and a pharmaceutically acceptable carrier, excipient or diluent.

As used herein, a "pharmaceutical composition" refers to a preparation of one or more of the active ingredients described herein, with other components such as physiologically suitable carriers and excipients. The purpose of a pharmaceutical composition is to facilitate administration of a compound to a subject.

Hereinafter, the phrases "therapeutically acceptable carrier" and "pharmaceutically acceptable carrier", which may be used interchangeably, refer to a carrier or a diluent that does not cause significant irritation to an organism and does not abrogate the biological activity and properties of the administered compound.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

In another embodiment of the present invention, a therapeutic composition further comprises a pharmaceutically acceptable carrier. As used herein, a "carrier" refers to any substance suitable as a vehicle for delivering of the agents or molecule of the present invention to a suitable in vivo or in vitro site. As such, carriers can act as a pharmaceutically acceptable excipient of a therapeutic composition of the present invention. Carriers of the present invention include: (1) excipients or formularies that transport, but do not specifically target a molecule to a cell (referred to herein as non-targeting carriers); and (2) excipients or formularies that deliver a molecule to a specific site in a subject or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Therapeutic compositions of the present invention can be sterilized by conventional methods.

Targeting carriers are herein referred to as "delivery vehicles". Delivery vehicles of the present invention are capable of delivering a therapeutic composition of the present invention to a target site in a subject. A "target site" refers to a site in a subject to which one desires to deliver a therapeutic composition. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in a subject, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a target cell can be introduced to the outer surface of a liposome delivery vehicle so as to target the delivery vehicle to the target cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

Therapeutic Use

According to some embodiments, the agents of the present invention are useful in regulating DAPk activity. Promoting DAPk activation is beneficial in the treatment of proliferative diseases such as cancer. Alternatively, inhibiting (or reducing) DAPk activity is beneficial in the treatment of pathologies associated with neuronal cell death.

According to some embodiments, the present invention is directed to a method for treating cancer in a subject in need thereof, comprising administering to the subject a pharmaceutical composition comprising a therapeutically effective amount of an agent capable of promoting DAPk activation.

In another embodiment, the invention provides a method for inhibiting tumor progression in a subject in need thereof, comprising administering to the subject a pharmaceutical composition comprising a therapeutically effective amount of an agent capable of promoting DAPk activation.

In another embodiment, there is provided a method for inducing tumor regression in a subject in need thereof, comprising administering to the subject a pharmaceutical composition comprising a therapeutically effective amount of an agent capable of promoting DAPk activation.

The compounds of the present invention are active against a wide range of cancers, including carcinomas, sarcomas, myelomas, leukemias, lymphomas and mixed type tumors. Particular categories of tumors amenable to treatment include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors amenable to treatment include: hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to certain embodiments, the cancer to be treated is selected from the group consisting of prostate cancer, breast cancer, skin cancer, colon cancer, lung cancer, pancreatic cancer, lymphoma, myeloma, leukemia, head and neck cancer, kidney cancer, ovarian cancer, bone cancer, liver cancer or thyroid cancer.

For example, in some embodiments, the tumor may include pediatric solid tumors, e.g., Wilms' tumor, hepatoblastoma and embryonal rhabdomyosarcoma, wherein each possibility represents a separate embodiment of the present invention. In other embodiments, the tumor includes, but is not limited to, germ cell tumors and trophoblastic tumors (e.g. testicular germ cell tumors, immature teratoma of the ovary, sacrococcygeal tumors, choriocarcinoma and placental site trophoblastic tumors), wherein each possibility represents a separate embodiment of the present invention. According to additional embodiments, the tumor includes, but is not limited to, epithelial adult tumors (e.g. bladder carcinoma, hepatocellular carcinoma, ovarian carcinoma, cervical carcinoma, lung carcinoma, breast carcinoma, squamous cell carcinoma in head and neck, colon carcinoma, renal cell carcinoma and esophageal carcinoma), wherein each possibility represents a separate embodiment of the present invention. In yet further embodiments, the tumor includes, but is not limited to, neurogenic tumors (e.g. astrocytoma, ganglioblastoma and neuroblastoma), wherein each possibility represents a separate embodiment of the present invention. In another embodiment, the tumor is prostate cancer. In another embodiment, the tumor is pancreatic cancer. In other embodiments, the tumor includes, for example, Ewing sarcoma, congenital mesoblastic nephroma, gastric adenocarcinoma, parotid gland adenoid cystic carcinoma, duodenal adenocarcinoma, T-cell leukemia and lymphoma, nasopharyngeal angiofibroma, melanoma, osteosarcoma, uterus cancer and non-small cell lung carcinoma, wherein each possibility represents a separate embodiment of the present invention.

In certain embodiments, the agents of the present invention can be used to treat cancer alone or in combination with other established or experimental therapeutic regimens against cancer. Therapeutic methods for treatment of cancer suitable for combination with the present invention include, but are not limited to, chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy, and photon beam radiosurgical therapy.

In another embodiment, tumors that may be treated according to the method of the present invention are those characterized by de-regulation of autophagy or de-regulation of autophagic function.

The methods of the invention are used to identify inhibitors of DAPk potentially useful for the treatment of a neurological condition. Neurological condition to be treated by the agents and pharmaceutical compositions comprising same, include neuronal cell death following acute insults such as hypoxia, ischemia, stroke, and trauma. Other neurological conditions treatable with agent of the invention include AIDS dementia, epilepsy, focal ischemia, Huntington's disease, Alzheimer's disease, Parkinson's disease, and amyotrophic lateral sclerosis. Each of these conditions is characterized by the progressive loss of a specific population of neurons in the central nervous system.

Screening Assays

The present invention provides screening assays for identifying agents that bind and modulate the activity of ROC domain of DAPk, thereby regulating the activity of DAPk. In some embodiments, the present invention provides screening assays for identifying agents that modulate the binding of GTP to the ROC domain of DAPk, thereby regulating the activity of DAPk.

In one embodiment, the method of screening described herein is a screening assay, such as a high-throughput screening assay. Thus, the contacting step can be in a cell-based or cell-free assay. For example, cells expressing DAPk can be contacted with a candidate agent either in vivo, ex vivo, or in vitro. The cells can be assayed in vitro or in situ or the protein extract of said cells can be assayed in vitro for the detection of activated DAPk. Cells can also be engineered to express a reporter construct, wherein the cells are contacted with a candidate agent and evaluated for reporter expression. Other such cell-based and cell-free assays are contemplated for use herein.

For example, the effect of small molecule, amino acid or nucleic acid mimetics on cancer cells or pathologic associated with neuronal cell death can be evaluated in cells expressing DAPk and compared to cells lacking DAPk.

In general, candidate (potential) agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein.

A potential agent may be a single, compound of interest or a member of a library of potential inhibitors. For example, a library of potential agents or molecules may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture). A library of potential agents can include, for example, amino acids, peptides, polypeptides, proteins (including, but not limited to, antibodies, antibody fragments and peptide aptamers), or fragments of peptides or proteins; nucleic acids (e.g., DNA; RNA; or peptide nucleic acids, PNA); aptamers; or compounds such as carbohydrates and polysaccharides. Each member of the library can be singular or can be a part of a mixture (e.g., a compressed library). The library can contain purified compounds or can be "dirty" (i.e., containing a significant quantity of impurities). Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) can also be used with the new methods.

Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods. In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effect should be employed whenever possible.

In addition to libraries of potential agents, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Peptide aptamers represent a novel generation of molecules in which variable peptides are inserted into a protein scaffold. As such, they can bind to their target in vivo and have the potential to selectively block its activity. Several bacterial proteins had been recently applied as scaffolds for peptide aptamers, including thioredoxin, staphylococcal nuclease and alpha-amylase, as well as non-bacterial proteins such as green fluorescent protein (Colas, 2000) (Hoppe-Seyler and Butz, 2000). The scaffold share intrinsic stability making it possible to express peptide aptamers in vivo at high concentrations, and, having the peptide aptamer been identified, utilize its high level expression and easy purification for subsequent analysis. Once identified, a peptide aptamer may be evaluated as a free peptide, where in some cases it is as active as in the context of the aptamer (Hoppe-Seyler and Butz, 2000). Moreover, small synthetic molecules may be derived from such bioactive aptamers to form the basis of new therapeutics.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits vascular permeability. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions in which it is desirable to regulate vascular permeability.

The potential agent may include, but are not limited to, peptides or proteins (either recombinant or naturally occurring), nucleic acids or other organic or inorganic compounds (e.g. carbohydrates and polysaccharides). In one embodiment, the potential inhibitors are peptide aptamers, comprising a peptide fused to a stabilizing protein. In another embodiment, the potential inhibitors are antibodies, antibody fragments including, but not limited to, single-chain antibodies (scFvs) and single antibody domain proteins (dAbs).

Having now generally described the invention, the same will be more readily understood through reference to the following examples, which are provided by way of illustration and are not intended to be limiting of the present invention.

EXAMPLES

Materials and Methods

Reagents

All Chemicals were purchased from Sigma-Aldrich unless otherwise indicated.

Cell Culture

Human embryonic kidney (HEK) 293T cells were grown in Dulbecco's modified Eagle's medium (Biological Industries, Beit Haemek, Israel) supplemented with 10% fetal bovine serum, 2 mM L-glutamine, 50 units/ml penicillin, and 50 µg/ml streptomycin (Invitrogen). Cells were transiently transfected by the calcium phosphate precipitation method.

Plasmids

Plasmids encoding N-terminal Flag and hemaglutinin (HA)-tagged human full-length DAPk (Flag-DAPk and HA-DAPk), HA-tagged DAPk lacking the cytoskeletal interacting region (ΔCyto—amino acids 641-835) and C-terminal Flag-tagged DAP1 have been described previously (Cohen, Feinstein et al. 1997; Koren, Reem et al. 2010). The plasmids pcDNA3 encoding the non-relevant protein luciferase and pEGFP-C1 encoding GFP were used as controls. Plasmids encoding DAPk mutants, HA-ΔROC (deletion between amino acids 667-954), HA-ΔKD (lacking amino acids 1-285) and HA-ΔP-Loop (deletion between amino acids 695-702) were generated by site directed mutagenesis using HA-DAPk as template. N-terminal Flag and HA-tagged DAPk ROC fragment (amino acids 667-954) were generated by PCR and ligation into the expression vector pcDNA3. Flag-tagged ROC fragment ΔP-Loop (lacking amino acids 695-702) was generated by site directed mutagenesis using Flag-ROC as template. The plasmid encoding GDP-bound state mimicking construct (DAPk T701N) was generated by site directed mutagenesis. Finally the plasmid pET3d-hMLC for expression of hMLC in bacteria was a gift of Mathias Gautel.

Western Blot Analysis

Total cell lysates or protein immunoprecipitates were resolved 10% polyacrylamide gels, transferred to nitrocellulose membranes blots, and incubated with monoclonal antibodies to Flag (Sigma), actin (Sigma) or HA (BAbCO). Secondary antibodies consisted of horseradish peroxidase-conjugated goat anti-mouse or anti-rabbit antibodies (Jackson ImmunoResearch Laboratories), which were detected by SuperSignal enhanced chemiluminescence (Pierce).

Protein Purification and Immunoprecipitation

Recombinant hMLC was expressed in BL21 (DE3) (Novagen) and purifications were carried out using the standard HiTrap Nickel affinity column (GE Healthcare). Different constructs were transfected in HEK 293T cells, which were lysed in G buffer (100 mM Tris-HCl, pH 7.5, 50 mM KCl, 5 mM $MgCl_2$, 0.1 mM DTT, 1 mM EDTA, 1% Triton X-100) supplemented with protease and phosphatase inhibitors cocktails. In order to immunopurify sufficient amounts of Flag-DAPk for size exclusion chromatography experiments, cells were first treated with the actin-depolymerizing agent latrunculin B (20 µM) for 45 min to release all of the kinase from the actin cytoskeleton, and then immediately lysed in G buffer. Extracts were immunoprecipitated with anti-FLAG M2 monoclonal antibody conjugated to protein G beads, and proteins were eluted with excess FLAG peptide.

GTP-Binding Assays

GTP-agarose beads (Sigma) were blocked with G buffer (100 mM Tris-HCl, pH 7.5, 50 mM KCl, 5 mM $MgCl_2$, 0.1 mM DTT, 1 mM EDTA, 1% Triton X-100) containing 100 µg/mL BSA for 1 h at 4° C. on rotator. Next, 100 µg of total cell lysates were incubated with the pre-treated GTP-agarose beads for 1 h at 4° C. on rotator. When indicated, GTP was added to a final concentration of 2 mM, followed by continuous incubation for additional 2 h. Then, the beads were washed three times with G buffer and the binding proteins eluted by addition of 40 µL 2×SDS sample buffer and boiling for 5 minutes. Eluted proteins were subjected to western blot analysis.

Analytic Size Exclusion Chromatography

Immunopurified Flag-DAPk was loaded onto an analytical Superdex™ 200 10/300 (GE Healthcare) gel-filtration column equilibrated with TBS. The eluting protein was detected by UV absorbance at 280 nm. Fractions were collected using the AKTA Prime fraction collector and analyzed by Western blot with anti-Flag antibodies. The migration position of the fractions containing Flag-DAPk was assigned relative to the migration position of Gel Filtration Calibration HMW standards (GE Healthcare) on the same column.

Kinase Assays

Maxisorp™ multiwell polystyrene plates (Nunc, Langenselbold, Germany) were incubated at 4° C., overnight, with the indicated amounts of hMLC diluted in PBS. Plates were washed with PBST and blocked with 4% BSA (Sigma, City, State) diluted in PBS. The kinase reactions were then performed on the plate. Briefly, the wells were incubated with kinase buffer (50 mM Hepes, pH 7.5, 20 mM $MgCl_2$, 0.1 mg/mL BSA, 50 mM β-glycerol phosphate, 50 µM ATP) containing 2.5 nM of the indicated enzyme, for 10 min. The reactions were stopped by addition of EDTA to final concentration of 25 mM. Plates were washed again with PBST and then incubated with rabbit anti MLC (Ser19) polyclonal antibody (Cell Signaling, Danvers, Mass.) at a 1:250 dilution in PBS. PBST wash was performed again and the plate incubated with HRP-conjugated goat anti rabbit IgG (Jackson ImmunoResearch, West Grove, Pa.). Detection was done with the HRP substrate ABTS. Where indicated the HRP read outs were plot using the Michaelis-Menten equation and the curves fit by the least squares method.

Cell Detachment Assays

Cell detachment was assessed as described before (Widau, Jin et al. 2010), by counting the adherent cells left in the tissue culture plate after 24 h of transfection with either DAPk WT or ΔP-Loop. Briefly, cells were washed twice in PBS to remove detached cells. Then, adherent cells were trypsinized and counted with a Countess® Automated Cell Counter (Invitrogen). The extent of cell detachment is defined as (the number of control cells—the number of treated cells)/(the number of control cells), where control cells are HEK 293T cell transected with the irrelevant protein luciferase.

Example 1

DAPk Homo-Oligomerizes in Cells

Many members of the ROCO protein family, including LRRK1 and LRRK2, form dimers in vivo (Greggio, Zambrano et al. 2008; Klein, Rovelli et al. 2009). Since DAPk was recently included as a member of the novel ROCO protein family, the possibility that DAPk might assemble into homodimers, was investigated.

Figure 1B:
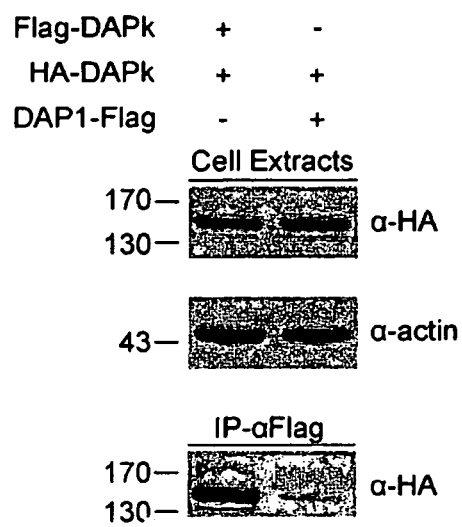

Differently tagged constructs of DAPk, namely HA-DAPk and Flag-DAPk, were prepared. HEK 293T cells were transiently co-transfected for 24 hours with either both constructs or with HA-DAPk only and cell lysates were subjected to immunoprecipitations with anti-Flag antibodies (IP-α Flag). Immune complexes were analyzed by western blot alongside aliquots of total cell extracts. Western blot analysis revealed the existence of HA-DAPk in the immune complexes formed by the anti-Flag antibodies only if the two DAPk constructs were co-expressed in the cells (FIG. 1A). This suggests that the two different constructs physically interact with each other forming stable complexes. In a similar experimental setting death-associated protein 1 (DAP1), which does not interact with DAPk (Kimchi, A. unpublished data) was used as a negative control (FIG. 1B). HEK 293T cells were co-transfected either with HA-DAPk and Flag-DAPk or HA-DAPk and DAP1-Flag. As seen in FIG. 1B, similar results were produced implying that the signal observed is not an artifact from non specific interactions with the Flag tag.

Figure 1C:
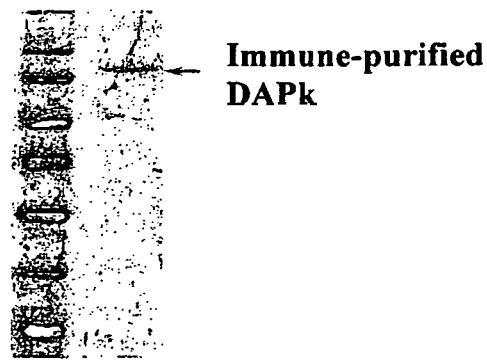
Figure 1D:
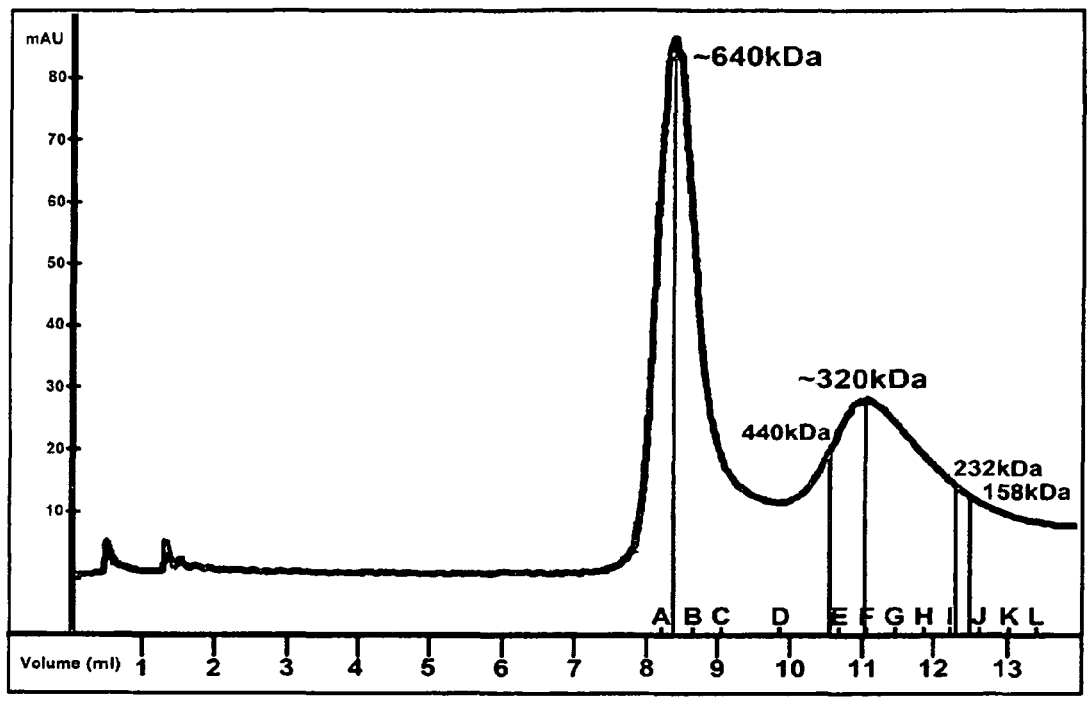
Figure 1E:

To determine the nature of DAPk homo-complexes in native non denatured conditions we performed a size exclusion chromatography analysis using immunopurified Flag-DAPk overexpressed in HEK 293T cells. Following injection into a Superdex™ 200 column connected to an ÄKTA™Fplc™ system, Flag-DAPk displayed a surprising profile. It elutes in two clearly defined peaks corresponding to ~640 kDa and ~320 kDa (FIG. 1D). Considering that full-length DAPk has a molecular weight of 160 kDa, this profile suggests that DAPk oligomerizes forming dimers and tetramers. Furthermore, the absence of a peak at the 160 kDa size range excluded the existence of monomers under native conditions. Fractions were collected at indicated elution points and submitted to western blot analysis, confirming DAPk identity at the selected peaks (FIG. 1E).

HEK 293T cells were transfected with Flag-DAPk. After lysis, cell extracts were immuneprecipitated with anti-Flag beads and Flag-DAPk was eluted by competition with Flag peptide. To test the purification status prior to column injection an aliquot of immunopurified Flag-DAPk was analyzed by SDS-PAGE stained with GelCode® Blue. The possibility of migration shifts due to interaction with other proteins is excluded by the relatively high degree of purification (≥90%) of the material loaded on the column (FIG. 1C).

Example 1 shows that DAPk homo-oligomerizes in cells and forms dimers and tetramers.

Example 2

The ROC and the Kinase Domains Mediate Homo-Oligomerization of DAPk

Figure 2A:
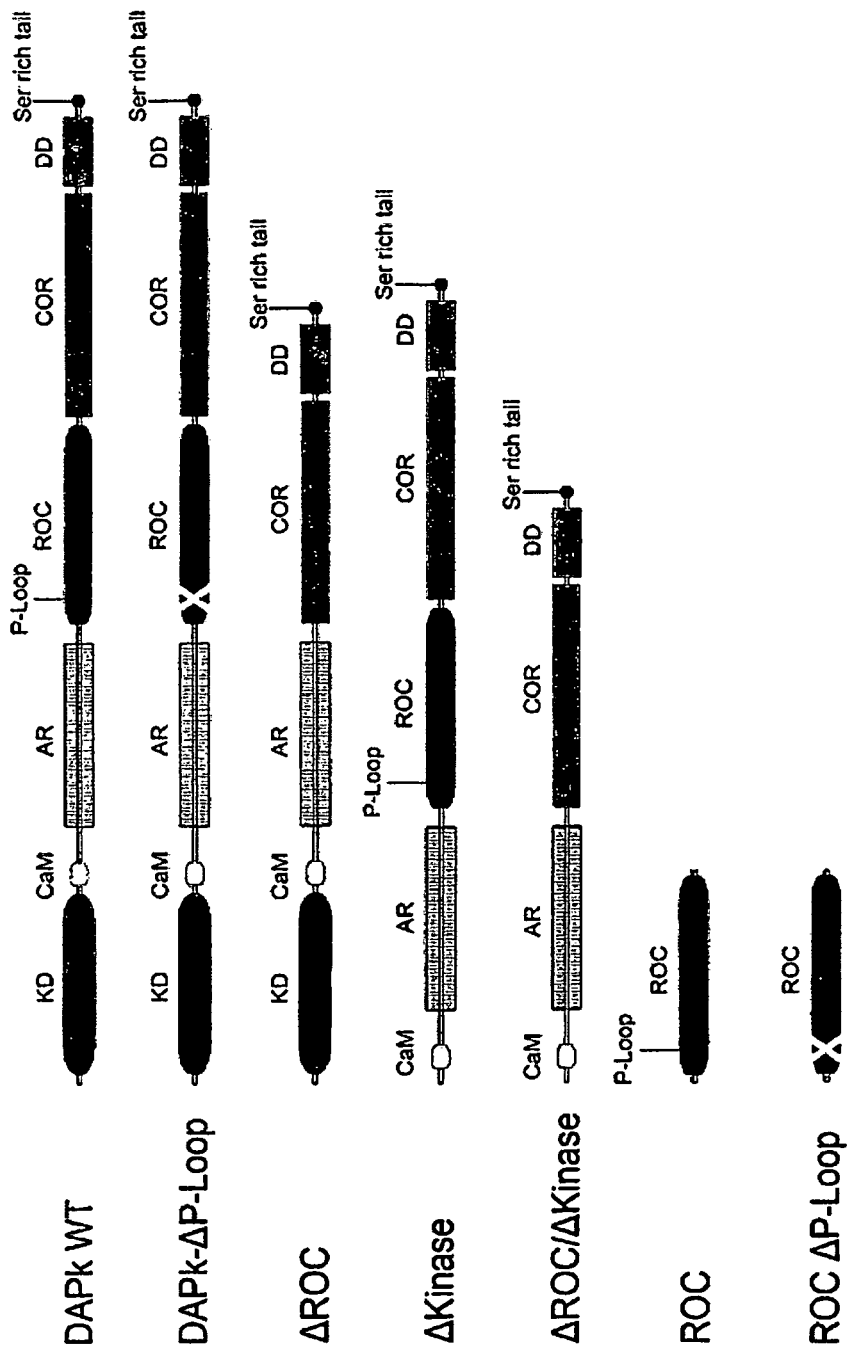
FIGS. 2A-D show that the ROC and Kinase domains are necessary for DAPk oligomerization.

The ROC domain has been shown to mediate homodimerization of LRRK2 and heterodimerization between DAPk and LRRK2 (Klein, Rovelli et al. 2009). Thus, the ability of DAPk to homodimerize in a ROC domain dependent manner was investigated either by expressing the ROC domain fragment by itself or by using constructs of DAPk deleted of the ROC domain. In these experiments HA and Flag tagged DAPk constructs were expressed in HEK 293T cells, and immunoprecipitated with anti-Flag antibodies. A schematic representation of the constructs utilized for these experiments can be seen in FIG. 2A.

Figure 2B:
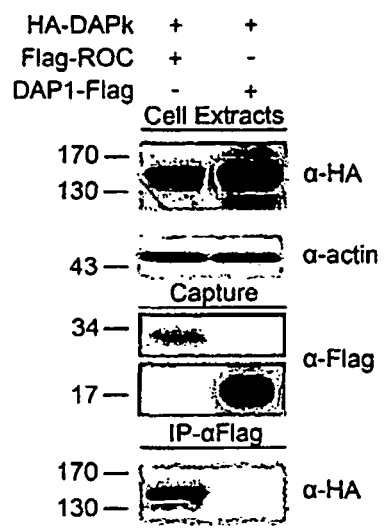
Figure 2D:
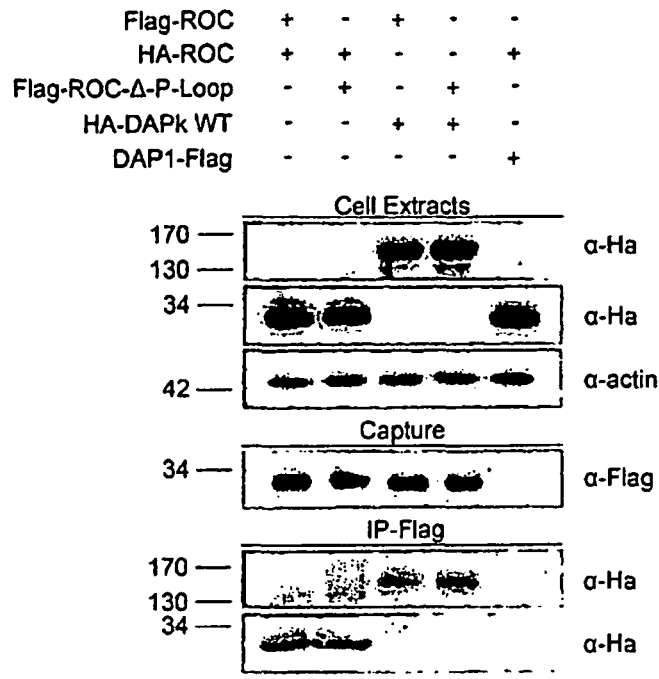
Figure 2C:
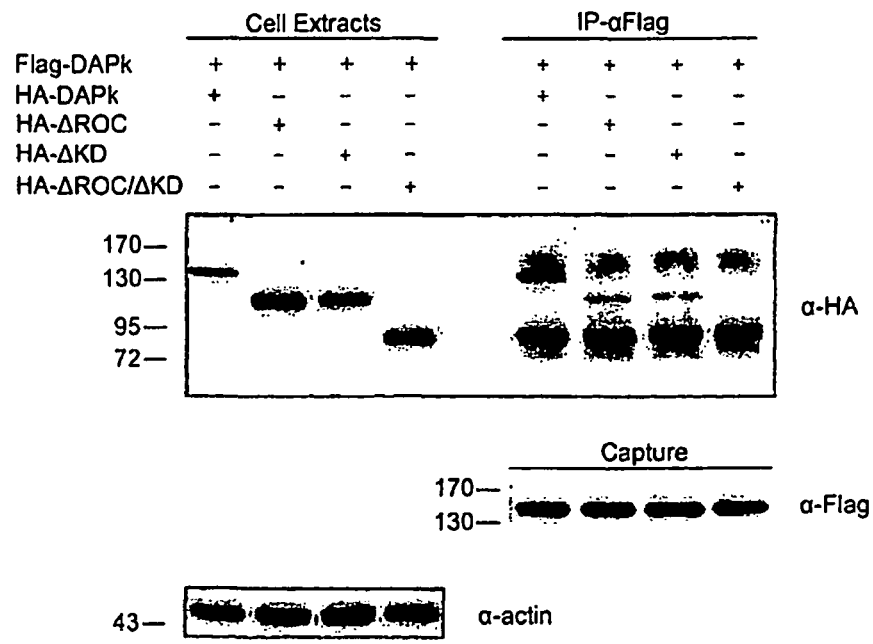

HEK 293T cells were co-transfected with HA-DAPk along with either Flag-ROC fragment (amino acids 667-954) or DAP1-Flag. Immunoprecipitation with anti-Flag beads (IP-α-Flag) was performed and immuno-complexes and cell extracts were analyzed by western blot. As seen in FIG. 2B, full length HA-DAPk (DAPk WT) significantly co-immunoprecipitated with Flag-ROC fragment, but not with DAP1, an irrelevant Flag-tagged control protein (DAP1-Flag). Thus, ROC fragment by itself is sufficient to bind the full length DAPk. Also the ROC fragments interacted with each other (FIG. 2D). Furthermore, the deletion of the ROC domain significantly reduced the interaction with the full length DAPk (FIG. 2C). Together the experiments in FIG. 2B-D established the role of the ROC domain in mediating homo-oligomerization.

Previous data showed that two members of the DAPk family, which share high sequence homology within their catalytic domains, interact with each other through this domain (Shani, Marash et al. 2004). Thus, the outcome of deletion of the kinase domain was tested. As seen in FIG. 2C, the deletion of the catalytic domain also interfered with the interaction with the full length DAPk. It was difficult to determine whether simultaneous deletion of both domains totally reduced the DAPk dimerization, as the double deletant migrated at the same position as a non-specific band on the western blot. Thus, the ROC domain is one of the interacting modules mediating homo-oligomerization of DAPk, in addition to the kinase domain which is also involved in this interaction.

The ROC domain contains a putative nucleotide binding site at its N-terminal end, known as the P-Loop. Considering the ROC domain involvement in DAPk homo-oligomerization, experiments were performed to check whether the P-Loop plays a role in this self interaction assembling process. A Flag tagged construct of the ROC fragment lacking only the 8 amino acids corresponding to the P-Loop motif (695-702) was prepared. Both HA tagged ROC fragment and DAPk WT underwent co-immunoprecipitaion with the P-Loop deletant to the same extent as they did with ROC fragment WT (FIG. 2D). This indicates that the P-Loop motif does not participate in DAPk homo-oligomerization.

Example 2 shows that the ROC and Kinase domains mediate homo-oligomerization of DAPk and are necessary for DAPk oligomerization.

Example 3

DAPk Binds GTP Through the P Loop Motif Located in the ROC Domain

Figure 3A:
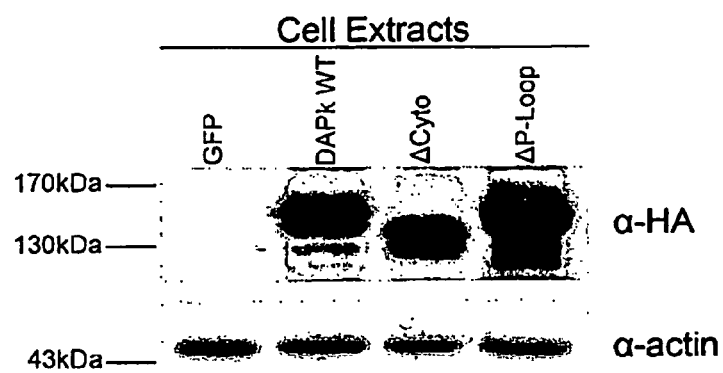
FIGS. 3A-B demonstrate that DAPk binds GTP via the P-Loop. Cell lysates expressing HA-DAPk WT, or deletion of the P-Loop (ΔP-loop) or cytoskeletal binding domain (ΔCyto), were incubated with GTP-agarose beads. Bound proteins were subjected to western blots with anti-HA antibody, after washing in the presence or absence of free GTP.
Figure 3B:
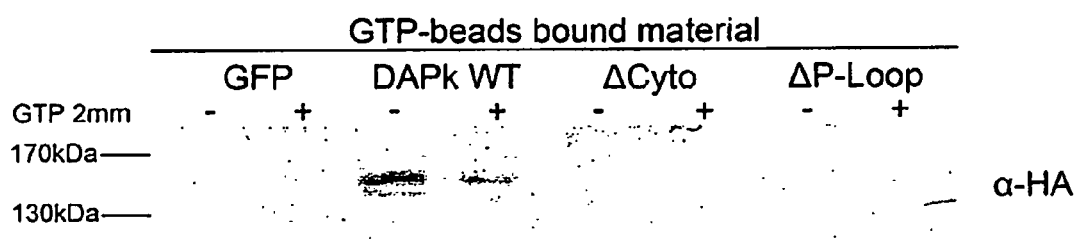

In order to assess whether the DAPk's putative P-Loop can bind GTP similar to other ROC containing proteins, lysates from HEK 293T cells over-expressing either DAPk WT or DAPk deleted of either the cytoskeletal binding domain (Δcyto—deleted of amino acids 645-844) or the P-Loop (ΔP-loop—deleted of amino acids 695-702) (FIG. 3A) were incubated with agarose beads conjugated to GTP. Bound proteins were washed in the presence or absence of free GTP, and eluted with protein sample buffer. Western blots analysis revealed that significantly, DAPk WT, but not the deletants, specifically bound GTP (FIG. 3B). Competition with the free GTP in the wash reduced this interaction, suggesting that the binding is GTP specific and not unspecific interaction with the agarose beads.

Example 3 shows that DAPk is a GTP-binding protein, and the P-loop is required for this specific interaction.

Example 4

GTP-Binding at the ROC Domain Attenuates the Enzymatic Activity of DAPk

Figure 4A:
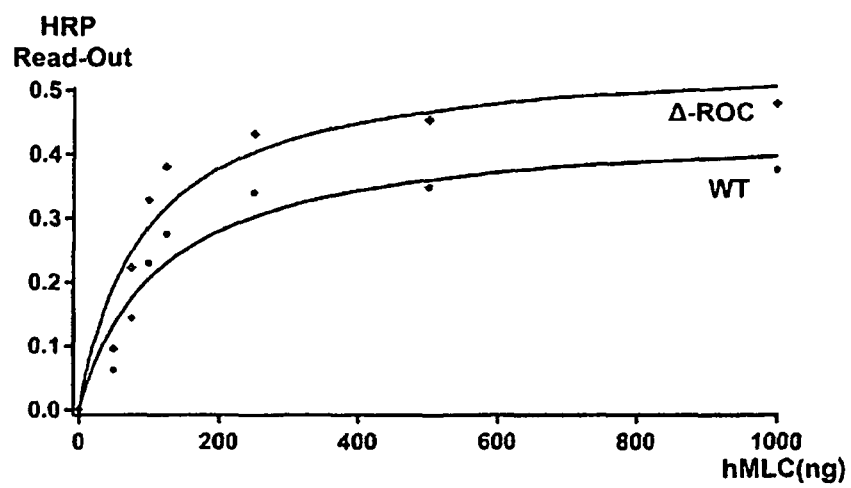
FIGS. 4A-D depicts in vitro kinase assays to assess the contribution of GTP binding to the catalytic activity of DAPk. The in vitro kinase assays were based on an ELISA format measuring phosphorylation of the DAPk substrate hMLC at Ser 19, using anti-phospho Ser19 antibodies.
Figure 4B:
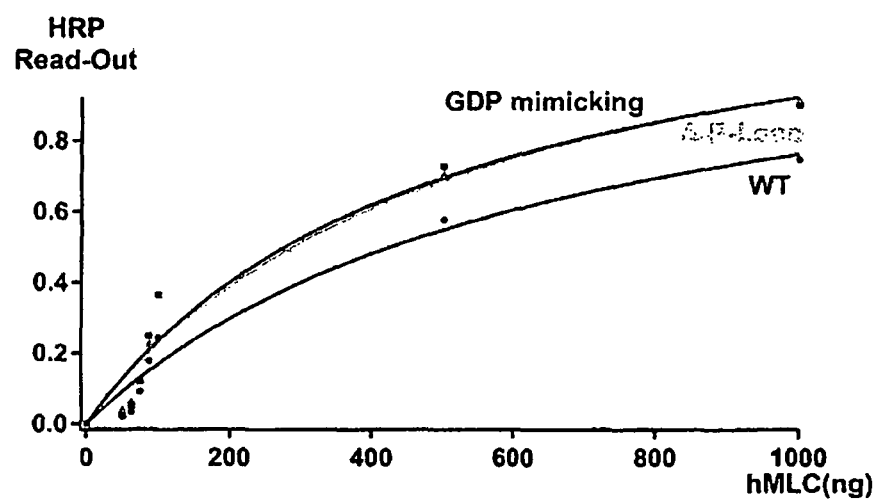

To determine the significance to DAPk's enzymatic activity of the ROC domain in general and of the GTP-binding in particular, in vitro kinase assays were performed. The assays were based on an ELISA format measuring phosphorylation of the DAPk substrate hMLC at Ser 19, using specific anti-phospho Ser19 antibodies. First, the activity of DAPk WT (FIG. 4A, WT) was compared to that of DAPk lacking the entire ROC domain (ΔROC—deleted of amino acids 667-954). As seen in FIG. 4A, the removal of the ROC domain resulted in increased kinase activity, which was evident by a higher $V_{max}$ value in a Michaelis-Menten kinetics plot (curves were fit using the method of the least squares). Similar results were observed with the ΔP-loop mutant and also with a GDP-bound state mimicking mutant (T701N) that abolishes GTP binding to the P-Loop (FIG. 4B). Thus, both strategies which prevent GTP binding increase the basal kinase activity.

Figure 4C:
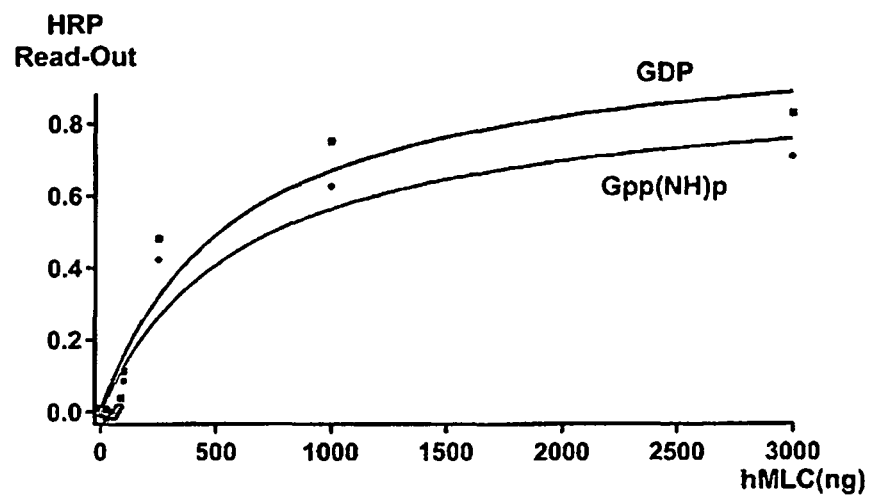
Figure 4D:
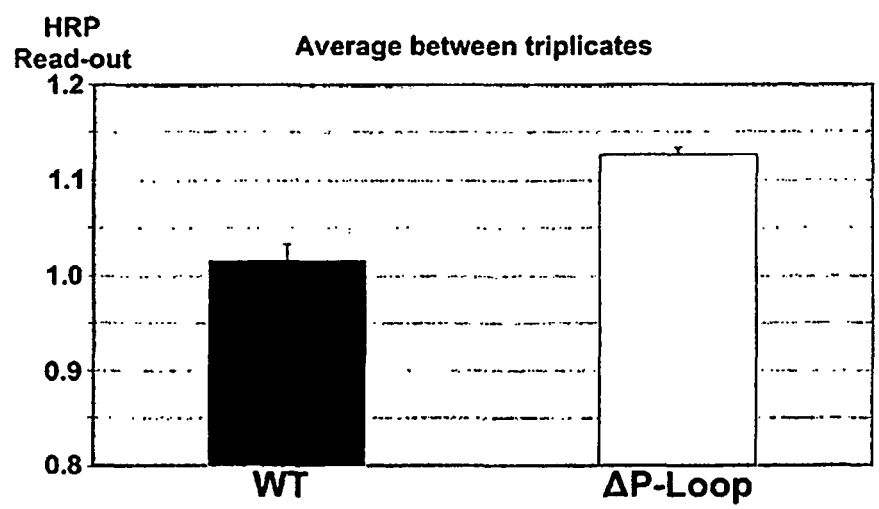

This was further confirmed by performing the kinase reaction in the presence of GDP or Gpp(NH)p, a non-hydrolysable GTP analog. DAPk-GDP showed increased catalytic activity compared to DAPk-GTP (FIG. 4C). Furthermore, under non-limiting hMLC concentrations DAPk ΔP-Loop is significantly more catalytic efficient than DAPk WT (FIG. 4D). Thus the ROC domain, specifically its GTP binding activity, functions to negatively regulate DAPk catalytic activity. The fact that a domain distant to the kinase domain can influence the basal catalytic activity of a CaM-activated kinase is a novel mode of regulation that has not been demonstrated before.

Example 4 shows that the ROC domain negatively regulates DAPk catalytic activity through binding to GTP, in a novel intra-molecular mode of regulation.

Example 5

Figure 5A:
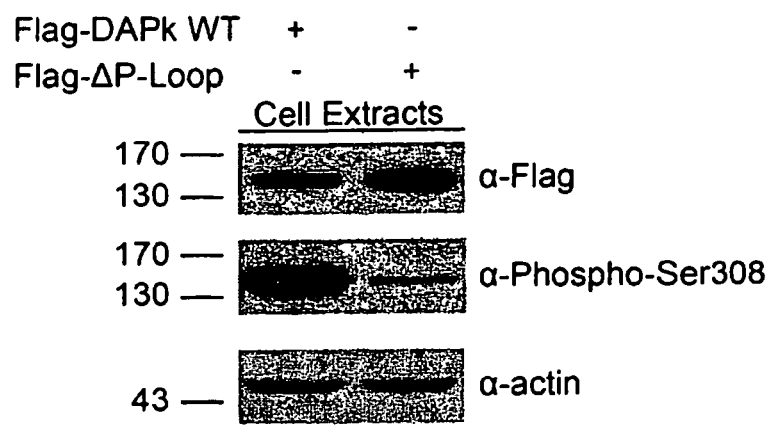
FIG. 5A-B demonstrates GTP binding at the P-Loop promoting Ser 308 negative autophosphorylation which occurs in cis.

GTP Binding at the P-Loop Promotes Ser 308 Negative Autophosphorylation in a Signaling Mode that Functions in cis The realization that GTP-binding to the P-Loop inhibits DAPk catalytic activity prompted further investigation to elucidate the mechanism by which such inhibition occurs. Therefore, the phosphorylation state of the Ser 308 of DAPk was assessed in cell lysates of HEK293T cells overexpressing either DAPk WT or ΔP-Loop mutant. Checking this specific phosphorylation site could indicate whether GTP-binding at the P-Loop modulates DAPk activity by a yet completely unknown mechanism or if it regulates the phosphorylation status of Ser 308, previously shown to exert auto-inhibitory effects on the catalytic activity. Interestingly, the Ser 308 of the ΔP-Loop mutant was significantly less phosphorylated than the WT counterpart (FIG. 5A). Thus, the fact that the ΔP-Loop mutant was consistently less phosphorylated explains its stronger activity in kinase assays. In addition, this result suggests that the GTP-binding imposes its inhibitory effect through regulating the phosphorylation state of the Ser 308, an already well established mechanism for controlling the DAPk catalytic activity (Shohat, Spivak-Kroizman et al. 2001).

The idea that a distant domain, namely the ROC domain, can regulate DAPk's catalytic activity by affecting the capability to undergo autophosphorylation indicates an unexpected novel intramolecular signal transduction mechanism for DAPk regulation. Yet, the fact that DAPk homo-oligomerizes, introduces another level of complexity. That is, a process that appears to be regulated in an intramolecular signal transduction fashion might easily be confounded with an intermolecular (in trans) mechanism. In the case of DAPk, since the kinase domain also mediates homo-oligomerization (FIG. 2C), it is extremely hard to uncouple kinase activity from oligomerization. Nevertheless, an experiment was designed to verify if the negative autophosphorylation at the Ser 308 occurs in cis or in trans considering the oligomeric state of DAPk in cells. To this end, HEK293T cells were co-transfected with DAPk kinase dead mutant (K42A) and increasing amounts of catalytic active GFP-DAPk. Then, cell extracts were analyzed by western blot for total DAPk and phosphorylated Ser 308 DAPk. Because of their difference in molecular weight, DAPk K42A and GFP-DAPk could be individually identified in the blots.

Figure 5B:
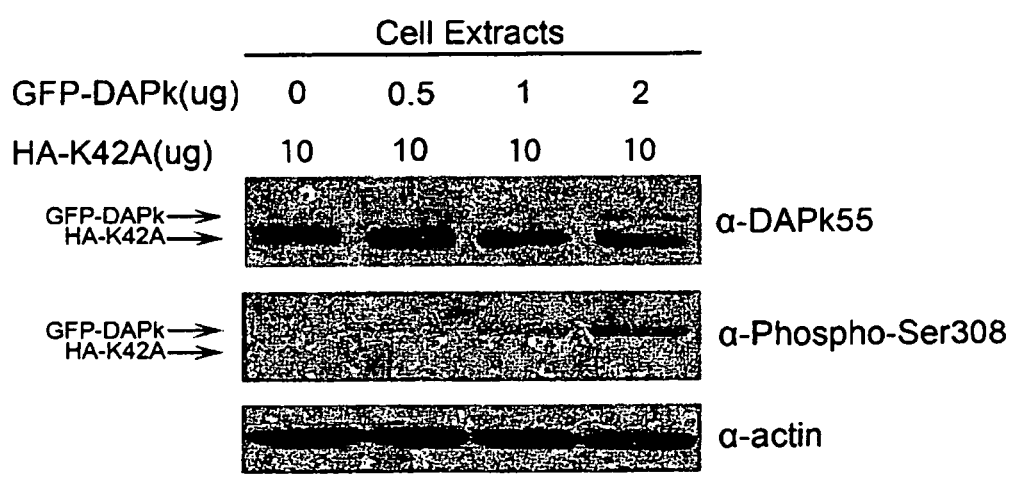

As expected for being a kinase dead construct, DAPk K42A does not display any phosphorylation at its Ser 308 when overexpressed alone in the cells (FIG. 5B). As the amounts of total GFP-DAPk increase by transfecting the cells with higher amounts of DNA, the phosphorylated Ser 308 corresponding to this construct increases too. Considering that the two constructs interact in vivo forming stable oligomers and if the negative autophosphorylation event at the Ser 308 occurred in trans we would expect the amounts of phosphorylated Ser 308 in DAPk K42A mutant to increase as the total GFP-DAPk increases. However, we detected no Ser 308 phosphorylation whatsoever in DAPk K42A mutant (FIG. 5B). This indicates that this important inhibitory autophosphorylation only occurs in cis and corroborates the hypothesis of GTP-mediated intramolecular signal transduction mechanism.

Example 5 shows that GTP binding at the P-Loop promotes Ser 308 intramolecular inhibitory autophosphorylation.

Example 6

Deletion of the DAPk P-Loop Motif Enhances DAPk's Cellular Activity

Figure 6A:
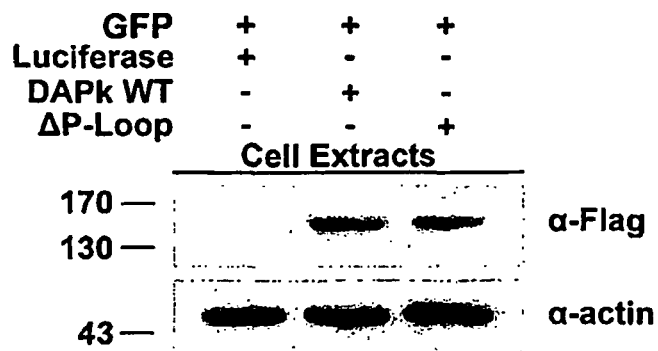
FIGS. 6A-C shows that GTP-binding to DAPk P-loop attenuates DAPk's functional activity. HEK 293T cells were co-transfected with free GFP and either DAPk WT, a construct deleted of the P-Loop motif (ΔP-loop), or with an irrelevant control protein (Luciferase).
Figure 6B:
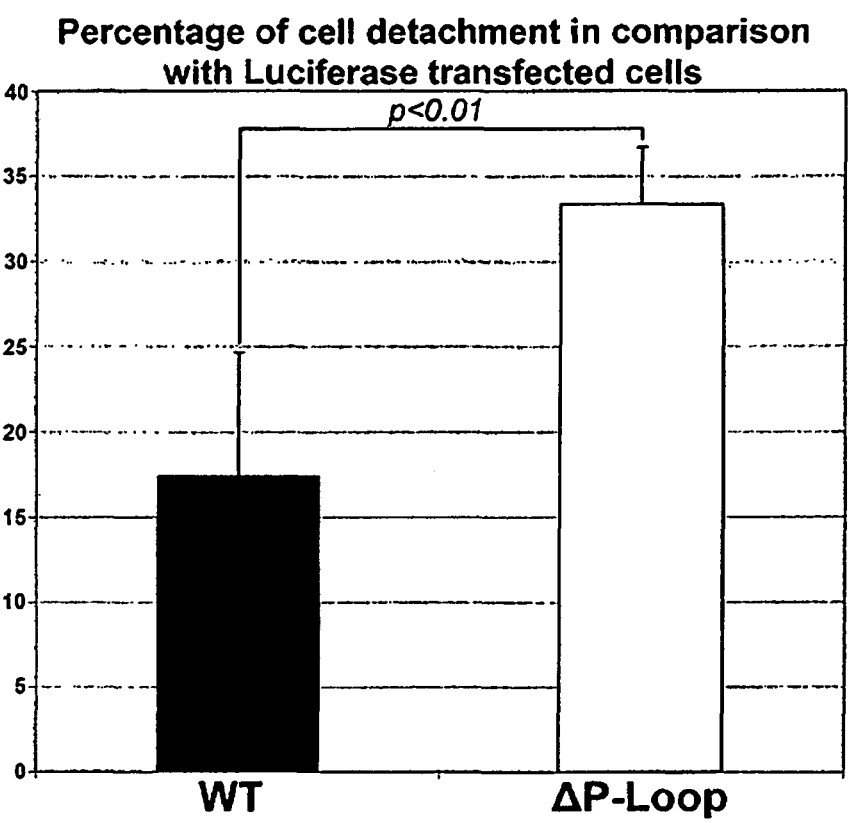
Figure 6C:
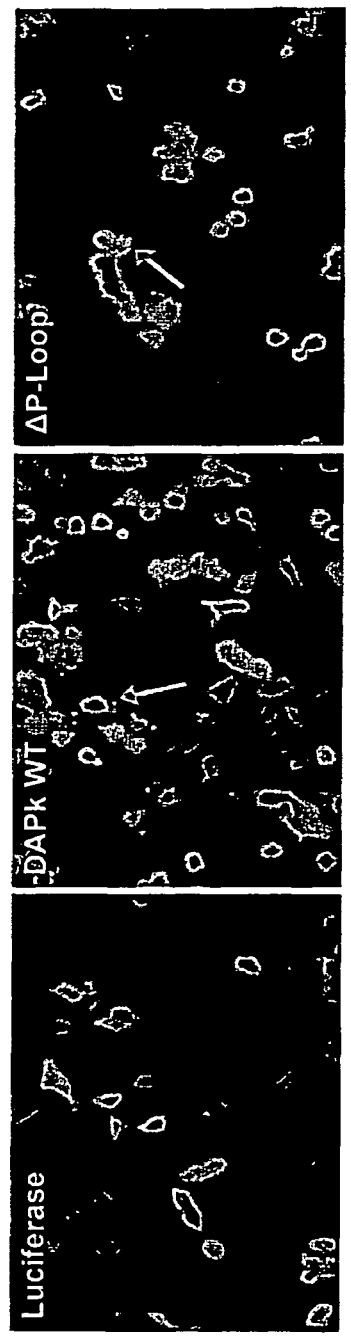

The functional effects of the GTP binding on DAPk's ability to induce some of its canonical phenotypic effects in cell cultures, namely cell rounding and detachment, and membrane blebbing, was assessed. These DAPk associated cellular changes are dependent on DAPk's catalytic activity and have been successfully used in other studies to assess DAPk activity in vivo (Widau, Jin et al. 2010). The necessity of the GTP-binding to the ROC domain for the extent of these effects on HEK 293T cells was examined. This was achieved by comparing DAPk WT to its P-Loop deletant counterpart. FIG. 6A presents a western blot analysis showing even expression levels between the constructs used in the cell detachment assay, ruling out any possibility of false results generated by uneven expression levels. Consistent with the increased kinase activity observed in vitro, ΔP-loop mutant led to increased cell detachment compared to the WT protein (33.3%±3.3%, 17.4%±7.4%, $p<0.01$) (FIG. 6B). Similarly, cells transfected with the ΔP-loop mutant presented more accentuated membrane blebbing than the cells that overexpressed the WT version of DAPk (FIG. 6C).

Example 6 indicates that GTP-binding negatively regulates DAPk's functional activity in vivo.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of screening for an agent for treating a pathology associated with neuronal cell death, comprising:
   (a) exposing in-vitro grown cells expressing death-associated protein kinase (DAPk) to a candidate agent;
   (b) extracting the cells under non-denaturing conditions;
   (c) detecting enhanced binding of GTP to the ROC domain of DAPk, as compared to in vitro grown cell not exposed to the agent, the enhanced binding of GTP to the ROC domain being indicative of inhibition of DAPk activity,
   (d) thereby identifying the agent as being capable of treating pathologies associated with neuronal cell death.

2. The method of claim 1, wherein said pathology associated with neuronal cell death is selected from the group consisting of: epilepsy, hypoxia/ischemia, acute brain injury, Parkinson's disease, Alzheimer's disease, Huntington's disease, AIDS, dementia and amyotrophic lateral sclerosis.

* * * * *

SEQUENCE LISTING

```
<160> NUMBER OF SEQ ID NOS: 3

<210> SEQ ID NO 1
<211> LENGTH: 255
<212> TYPE: PRT
<213> ORGANISM: Homo sapiens

<400> SEQUENCE: 1

Lys Asp Thr His Arg Gly Leu Phe Ile Gln Gln Leu Arg Pro Thr Gln
1               5                   10                  15

Asn Leu Gln Pro Arg Ile Lys Leu Lys Leu Phe Gly His Ser Gly Ser
            20                  25                  30

Gly Lys Thr Thr Leu Val Glu Ser Leu Lys Cys Gly Leu Leu Arg Ser
        35                  40                  45

Phe Phe Arg Arg Arg Pro Arg Leu Ser Ser Thr Asn Ser Ser Arg
    50                  55                  60

Phe Pro Pro Ser Pro Leu Ala Ser Lys Pro Thr Val Ser Val Ser Ile
65                  70                  75                  80
```

```
Asn Asn Leu Tyr Pro Gly Cys Glu Asn Val Ser Val Arg Ser Arg Ser
                 85                  90                  95

Met Met Phe Glu Pro Gly Leu Thr Lys Gly Met Leu Glu Val Phe Val
            100                 105                 110

Ala Pro Thr His His Pro His Cys Ser Ala Asp Asp Gln Ser Thr Lys
        115                 120                 125

Ala Ile Asp Ile Gln Asn Ala Tyr Leu Asn Gly Val Gly Asp Phe Ser
    130                 135                 140

Val Trp Glu Phe Ser Gly Asn Pro Val Tyr Phe Cys Cys Tyr Asp Tyr
145                 150                 155                 160

Phe Ala Ala Asn Asp Pro Thr Ser Ile His Val Val Phe Ser Leu
                165                 170                 175

Glu Glu Pro Tyr Glu Ile Gln Leu Asn Gln Val Ile Phe Trp Leu Ser
            180                 185                 190

Phe Leu Lys Ser Leu Val Pro Val Glu Glu Pro Ile Ala Phe Gly Gly
        195                 200                 205

Lys Leu Lys Asn Pro Leu Gln Val Val Leu Val Ala Thr His Ala Asp
    210                 215                 220

Ile Met Asn Val Pro Arg Pro Ala Gly Gly Glu Phe Gly Tyr Asp Lys
225                 230                 235                 240

Asp Thr Ser Leu Leu Lys Glu Ile Arg Asn Arg Phe Gly Asn Asp
                245                 250                 255

<210> SEQ ID NO 2
<211> LENGTH: 9
<212> TYPE: PRT
<213> ORGANISM: Homo sapiens

<400> SEQUENCE: 2

Gly His Ser Gly Ser Gly Lys Thr Thr
1               5

<210> SEQ ID NO 3
<211> LENGTH: 1430
<212> TYPE: PRT
<213> ORGANISM: Homo sapiens

<400> SEQUENCE: 3

Met Thr Val Phe Arg Gln Glu Asn Val Asp Asp Tyr Tyr Asp Thr Gly
1               5                   10                  15

Glu Glu Leu Gly Ser Gly Gln Phe Ala Val Val Lys Lys Cys Arg Glu
            20                  25                  30

Lys Ser Thr Gly Leu Gln Tyr Ala Ala Lys Phe Ile Lys Lys Arg Arg
        35                  40                  45

Thr Lys Ser Ser Arg Arg Gly Val Ser Arg Glu Asp Ile Glu Arg Glu
    50                  55                  60

Val Ser Ile Leu Lys Glu Ile Gln His Pro Asn Val Ile Thr Leu His
65                  70                  75                  80

Glu Val Tyr Glu Asn Lys Thr Asp Val Ile Leu Ile Leu Glu Leu Val
                85                  90                  95

Ala Gly Gly Glu Leu Phe Asp Phe Leu Ala Glu Lys Glu Ser Leu Thr
            100                 105                 110

Glu Glu Glu Ala Thr Glu Phe Leu Lys Gln Ile Leu Asn Gly Val Tyr
        115                 120                 125

Tyr Leu His Ser Leu Gln Ile Ala His Phe Asp Leu Lys Pro Glu Asn
    130                 135                 140
```

-continued

```
Ile Met Leu Leu Asp Arg Asn Val Pro Lys Pro Arg Ile Lys Ile Ile
145                 150                 155                 160

Asp Phe Gly Leu Ala His Lys Ile Asp Phe Gly Asn Glu Phe Lys Asn
                165                 170                 175

Ile Phe Gly Thr Pro Glu Phe Val Ala Pro Glu Ile Val Asn Tyr Glu
            180                 185                 190

Pro Leu Gly Leu Glu Ala Asp Met Trp Ser Ile Gly Val Ile Thr Tyr
        195                 200                 205

Ile Leu Leu Ser Gly Ala Ser Pro Phe Leu Gly Asp Thr Lys Gln Glu
    210                 215                 220

Thr Leu Ala Asn Val Ser Ala Val Asn Tyr Glu Phe Glu Asp Glu Tyr
225                 230                 235                 240

Phe Ser Asn Thr Ser Ala Leu Ala Lys Asp Phe Ile Arg Arg Leu Leu
                245                 250                 255

Val Lys Asp Pro Lys Lys Arg Met Thr Ile Gln Asp Ser Leu Gln His
            260                 265                 270

Pro Trp Ile Lys Pro Lys Asp Thr Gln Gln Ala Leu Ser Arg Lys Ala
        275                 280                 285

Ser Ala Val Asn Met Glu Lys Phe Lys Lys Phe Ala Ala Arg Lys Lys
    290                 295                 300

Trp Lys Gln Ser Val Arg Leu Ile Ser Leu Cys Gln Arg Leu Ser Arg
305                 310                 315                 320

Ser Phe Leu Ser Arg Ser Asn Met Ser Val Ala Arg Ser Asp Asp Thr
                325                 330                 335

Leu Asp Glu Glu Asp Ser Phe Val Met Lys Ala Ile Ile His Ala Ile
            340                 345                 350

Asn Asp Asp Asn Val Pro Gly Leu Gln His Leu Leu Gly Ser Leu Ser
        355                 360                 365

Asn Tyr Asp Val Asn Gln Pro Asn Lys His Gly Thr Pro Pro Leu Leu
    370                 375                 380

Ile Ala Ala Gly Cys Gly Asn Ile Gln Ile Leu Gln Leu Leu Ile Lys
385                 390                 395                 400

Arg Gly Ser Arg Ile Asp Val Gln Asp Lys Gly Gly Ser Asn Ala Val
                405                 410                 415

Tyr Trp Ala Ala Arg His Gly His Val Asp Thr Leu Lys Phe Leu Ser
            420                 425                 430

Glu Asn Lys Cys Pro Leu Asp Val Lys Asp Lys Ser Gly Glu Met Ala
        435                 440                 445

Leu His Val Ala Ala Arg Tyr Gly His Ala Asp Val Ala Gln Leu Leu
    450                 455                 460

Cys Ser Phe Gly Ser Asn Pro Asn Ile Gln Asp Lys Glu Glu Glu Thr
465                 470                 475                 480

Pro Leu His Cys Ala Ala Trp His Gly Tyr Tyr Ser Val Ala Lys Ala
                485                 490                 495

Leu Cys Glu Ala Gly Cys Asn Val Asn Ile Lys Asn Arg Glu Gly Glu
            500                 505                 510

Thr Pro Leu Leu Thr Ala Ser Ala Arg Gly Tyr His Asp Ile Val Glu
        515                 520                 525

Cys Leu Ala Glu His Gly Ala Asp Leu Asn Ala Cys Asp Lys Asp Gly
    530                 535                 540

His Ile Ala Leu His Leu Ala Val Arg Arg Cys Gln Met Glu Val Ile
545                 550                 555                 560

Lys Thr Leu Leu Ser Gln Gly Cys Phe Val Asp Tyr Gln Asp Arg His
```

```
                565                 570                 575
Gly Asn Thr Pro Leu His Val Ala Cys Lys Asp Gly Asn Met Pro Ile
            580                 585                 590

Val Val Ala Leu Cys Glu Ala Asn Cys Asn Leu Asp Ile Ser Asn Lys
            595                 600                 605

Tyr Gly Arg Thr Pro Leu His Leu Ala Ala Asn Asn Gly Ile Leu Asp
            610                 615                 620

Val Val Arg Tyr Leu Cys Leu Met Gly Ala Ser Val Glu Ala Leu Thr
625                 630                 635                 640

Thr Asp Gly Lys Thr Ala Glu Asp Leu Ala Arg Ser Glu Gln His Glu
            645                 650                 655

His Val Ala Gly Leu Leu Ala Arg Leu Arg Lys Asp Thr His Arg Gly
            660                 665                 670

Leu Phe Ile Gln Gln Leu Arg Pro Thr Gln Asn Leu Gln Pro Arg Ile
            675                 680                 685

Lys Leu Lys Leu Phe Gly His Ser Gly Ser Gly Lys Thr Thr Leu Val
            690                 695                 700

Glu Ser Leu Lys Cys Gly Leu Leu Arg Ser Phe Phe Arg Arg Arg Arg
705                 710                 715                 720

Pro Arg Leu Ser Ser Thr Asn Ser Ser Arg Phe Pro Ser Pro Leu
            725                 730                 735

Ala Ser Lys Pro Thr Val Ser Val Ser Ile Asn Asn Leu Tyr Pro Gly
            740                 745                 750

Cys Glu Asn Val Ser Val Arg Ser Arg Ser Met Met Phe Glu Pro Gly
            755                 760                 765

Leu Thr Lys Gly Met Leu Glu Val Phe Val Ala Pro Thr His His Pro
770                 775                 780

His Cys Ser Ala Asp Asp Gln Ser Thr Lys Ala Ile Asp Ile Gln Asn
785                 790                 795                 800

Ala Tyr Leu Asn Gly Val Gly Asp Phe Ser Val Trp Glu Phe Ser Gly
            805                 810                 815

Asn Pro Val Tyr Phe Cys Cys Tyr Asp Tyr Phe Ala Ala Asn Asp Pro
            820                 825                 830

Thr Ser Ile His Val Val Phe Ser Leu Glu Glu Pro Tyr Glu Ile
            835                 840                 845

Gln Leu Asn Gln Val Ile Phe Trp Leu Ser Phe Leu Lys Ser Leu Val
            850                 855                 860

Pro Val Glu Glu Pro Ile Ala Phe Gly Gly Lys Leu Lys Asn Pro Leu
865                 870                 875                 880

Gln Val Val Leu Val Ala Thr His Ala Asp Ile Met Asn Val Pro Arg
            885                 890                 895

Pro Ala Gly Gly Glu Phe Gly Tyr Asp Lys Asp Thr Ser Leu Leu Lys
            900                 905                 910

Glu Ile Arg Asn Arg Phe Gly Asn Asp Leu His Ile Ser Asn Lys Leu
            915                 920                 925

Phe Val Leu Asp Ala Gly Ala Ser Gly Ser Lys Asp Met Lys Val Leu
            930                 935                 940

Arg Asn His Leu Gln Glu Ile Arg Ser Gln Ile Val Ser Val Cys Pro
945                 950                 955                 960

Pro Met Thr His Leu Cys Glu Lys Ile Ile Ser Thr Leu Pro Ser Trp
            965                 970                 975

Arg Lys Leu Asn Gly Pro Asn Gln Leu Met Ser Leu Gln Gln Phe Val
            980                 985                 990
```

```
Tyr Asp Val Gln Asp Gln Leu Asn  Pro Leu Ala Ser Glu  Glu Asp Leu
            995              1000                1005

Arg Arg  Ile Ala Gln Gln Leu  His Ser Thr Gly Glu  Ile Asn Ile
    1010              1015              1020

Met Gln  Ser Glu Thr Val Gln  Asp Val Leu Leu Leu  Asp Pro Arg
    1025              1030              1035

Trp Leu  Cys Thr Asn Val Leu  Gly Lys Leu Leu Ser  Val Glu Thr
    1040              1045              1050

Pro Arg  Ala Leu His His Tyr  Arg Gly Arg Tyr Thr  Val Glu Asp
    1055              1060              1065

Ile Gln  Arg Leu Val Pro Asp  Ser Asp Val Glu Glu  Leu Leu Gln
    1070              1075              1080

Ile Leu  Asp Ala Met Asp Ile  Cys Ala Arg Asp Leu  Ser Ser Gly
    1085              1090              1095

Thr Met  Val Asp Val Pro Ala  Leu Ile Lys Thr Asp  Asn Leu His
    1100              1105              1110

Arg Ser  Trp Ala Asp Glu Glu  Asp Glu Val Met Val  Tyr Gly Gly
    1115              1120              1125

Val Arg  Ile Val Pro Val Glu  His Leu Thr Pro Phe  Pro Cys Gly
    1130              1135              1140

Ile Phe  His Lys Val Gln Val  Asn Leu Cys Arg Trp  Ile His Gln
    1145              1150              1155

Gln Ser  Thr Glu Gly Asp Ala  Asp Ile Arg Leu Trp  Val Asn Gly
    1160              1165              1170

Cys Lys  Leu Ala Asn Arg Gly  Ala Glu Leu Leu Val  Leu Leu Val
    1175              1180              1185

Asn His  Gly Gln Gly Ile Glu  Val Gln Val Arg Gly  Leu Glu Thr
    1190              1195              1200

Glu Lys  Ile Lys Cys Cys Leu  Leu Leu Asp Ser Val  Cys Ser Thr
    1205              1210              1215

Ile Glu  Asn Val Met Ala Thr  Thr Leu Pro Gly Leu  Leu Thr Val
    1220              1225              1230

Lys His  Tyr Leu Ser Pro Gln  Gln Leu Arg Glu His  His Glu Pro
    1235              1240              1245

Val Met  Ile Tyr Gln Pro Arg  Asp Phe Phe Arg Ala  Gln Thr Leu
    1250              1255              1260

Lys Glu  Thr Ser Leu Thr Asn  Thr Met Gly Gly Tyr  Lys Glu Ser
    1265              1270              1275

Phe Ser  Ser Ile Met Cys Phe  Gly Cys His Asp Val  Tyr Ser Gln
    1280              1285              1290

Ala Ser  Leu Gly Met Asp Ile  His Ala Ser Asp Leu  Asn Leu Leu
    1295              1300              1305

Thr Arg  Arg Lys Leu Ser Arg  Leu Leu Asp Pro Pro  Asp Pro Leu
    1310              1315              1320

Gly Lys  Asp Trp Cys Leu Leu  Ala Met Asn Leu Gly  Leu Pro Asp
    1325              1330              1335

Leu Val  Ala Lys Tyr Asn Thr  Ser Asn Gly Ala Pro  Lys Asp Phe
    1340              1345              1350
```

-continued

```
Leu Pro Ser Pro Leu His Ala Leu Leu Arg Glu Trp Thr Thr Tyr
    1355            1360                1365

Pro Glu Ser Thr Val Gly Thr Leu Met Ser Lys Leu Arg Glu Leu
    1370            1375                1380

Gly Arg Arg Asp Ala Ala Asp Phe Leu Leu Lys Ala Ser Ser Val
    1385            1390                1395

Phe Lys Ile Asn Leu Asp Gly Asn Gly Gln Glu Ala Tyr Ala Ser
    1400            1405                1410

Ser Cys Asn Ser Gly Thr Ser Tyr Asn Ser Ile Ser Ser Val Val
    1415            1420                1425

Ser Arg
    1430
```